(12) United States Patent
Srivastava et al.

(10) Patent No.: US 9,441,002 B2
(45) Date of Patent: Sep. 13, 2016

(54) DITHIOLANE BASED THIOL MODIFIER FOR LABELING AND STRONGER IMMOBILIZATION OF BIO-MOLECULES ON SOLID SURFACES

(71) Applicant: ChemGenes Corporation, Wilmington, MA (US)

(72) Inventors: Suresh C. Srivastava, Burlington, MA (US); Santhosh Kumar Thatikonda, Woburn, MA (US); Sant K. Srivastav, Burlington, MA (US); Praveen K. Shukla, Burlington, MA (US); Alok Srivastava, Burlington, MA (US)

(73) Assignee: ChemGenes Corporation, Wilmington, MA (US)

( * ) Notice: Subject to any disclaimer, the term of this patent is extended or adjusted under 35 U.S.C. 154(b) by 143 days.

(21) Appl. No.: 14/065,385

(22) Filed: Oct. 28, 2013

(65) Prior Publication Data

US 2014/0142253 A1    May 22, 2014

Related U.S. Application Data

(60) Provisional application No. 61/795,851, filed on Oct. 27, 2012.

(51) Int. Cl.
| | |
|---|---|
| *C08F 8/34* | (2006.01) |
| *C07H 21/00* | (2006.01) |
| *C07H 19/04* | (2006.01) |
| *C07D 327/04* | (2006.01) |
| *C07F 9/6553* | (2006.01) |
| *C07F 9/24* | (2006.01) |

(52) U.S. Cl.
CPC ....... *C07F 9/655345* (2013.01); *C07F 9/2408* (2013.01); *C07H 21/00* (2013.01)

(58) Field of Classification Search
CPC . C07F 9/2408; C07F 9/655345; C07H 21/00
USPC ................ 525/333.5; 536/25.31, 26.5; 549/7
See application file for complete search history.

(56) References Cited

U.S. PATENT DOCUMENTS

2003/0044402 A1*   3/2003   Nelson ................. A61K 31/385
                                                              424/94.6

* cited by examiner

*Primary Examiner* — William Cheung
(74) *Attorney, Agent, or Firm* — Harvest IP Law LLP

(57) ABSTRACT

The thiol modified oligonucleotides have vast number of applications in the field of nucleic acid chemistry. The conjugates generated by mono thiol groups are unstable at higher temperature, in high salt concentration buffers and in presence other thiols. There is strong need to develop a novel thiol modifier probes that can generate multiple thiol groups. Described herein are efficient processes and compounds, dithiolane phosphoramidites derivative and dithiolane succinyl supports. The advantage of our cyclic disulfide thiol modifier is multifold a) each incorporation introduces two thiol groups; b) it can be introduced at any desired site of oligonucleotides; c) The symmetrical branching nature of the spacer in the linker arm of dithiolane allows for clean oligo synthesis, where cleavage of the linker arm and thereby of loss of oligo chain is prevented. We have successfully made 20-mer oligonucleotide containing single dithiolane derivative at 3', and 21-mer oligonucleotides containing single dithiolane derivative at 5' or in the middle of the mixed base sequence. HPLC and ESI MS analysis of these oligonucleotides indicated satisfactory purity and correct composition of these oligos, respectively.

4 Claims, 21 Drawing Sheets

HPLC purity analysis of the 6-amino-2-((bis(4-methoxyphenyl)(phenyl)methoxy)methyl)hexan-1-ol compound 6

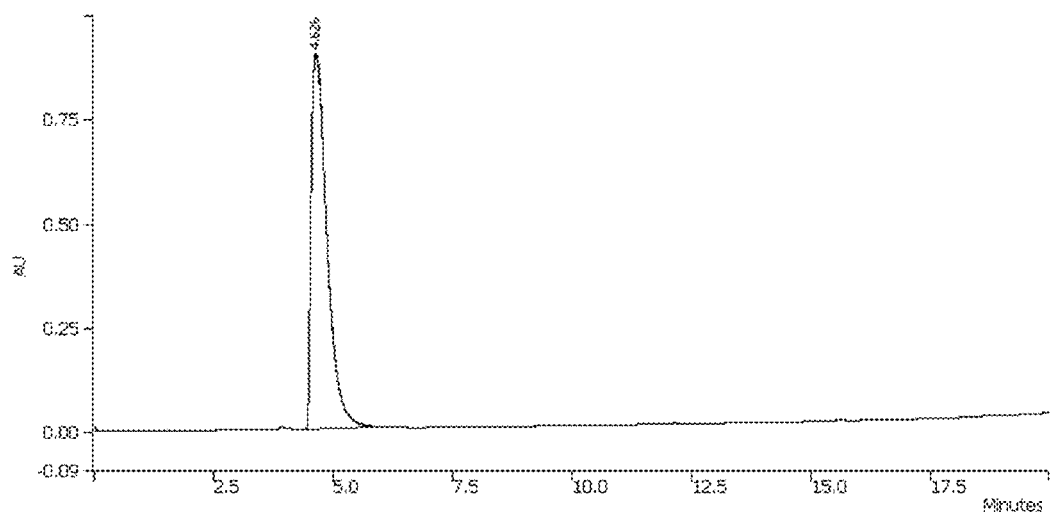
Figure 1: HPLC purity analysis of the 6-amino-2-((bis(4-methoxyphenyl)(phenyl)methoxy)methyl)hexan-1-ol compound 6
| Peak No | Peak Name | Ret Time (min) | Peak Area (counts) | Result (Area %) |
|---|---|---|---|---|
| 1 | | 2.639 | 77996 | 0.04 |
| 2 | | 3.912 | 688221 | 0.33 |
| 3 | | 4.626 | 209142096 | 99.34 |
| 4 | | 7.244 | 41858 | 0.02 |
| 5 | | 12.150 | 277359 | 0.13 |
| 6 | | 15.587 | 297656 | 0.14 |
| | Totals | | 210525184 | 100.00 |
Figure 2: HPLC table peaks of the 6-amino-2-((bis(4-methoxyphenyl)(phenyl)methoxy)methyl)hexan-1-ol compound 6

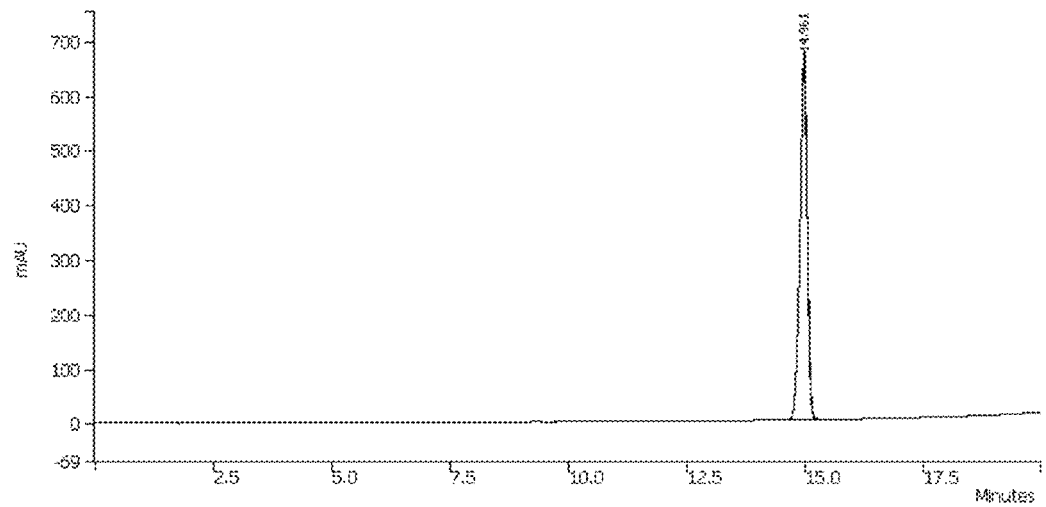
Figure 3: HPLC purity analysis of the *N*-(6-(bis(4-methoxyphenyl)(phenyl)methoxy)-5-(hydroxymethyl)hexyl)-5-(1,2-dithiolan-3-yl)pentanamide compound 7.
| Peak No | Peak Name | Ret Time (min) | Peak Area (counts) | Result (Area %) |
|---|---|---|---|---|
| 1 | | 5.435 | 16915 | 0.02 |
| 2 | | 6.863 | 15668 | 0.02 |
| 3 | | 9.307 | 80350 | 0.11 |
| 4 | | 10.271 | 45587 | 0.06 |
| 5 | | 14.961 | 71611400 | 99.48 |
| 6 | | 16.367 | 23782 | 0.03 |
| 7 | | 17.049 | 123471 | 0.17 |
| 8 | | 17.457 | 16870 | 0.02 |
| 9 | | 18.153 | 50857 | 0.07 |
| | Totals | | 71984904 | 99.98 |
Figure 4: HPLC table peaks of the *N*-(6-(bis(4-methoxyphenyl)(phenyl)methoxy)-5-(hydroxymethyl)hexyl)-5-(1,2-dithiolan-3-yl)pentanamide compound 7.

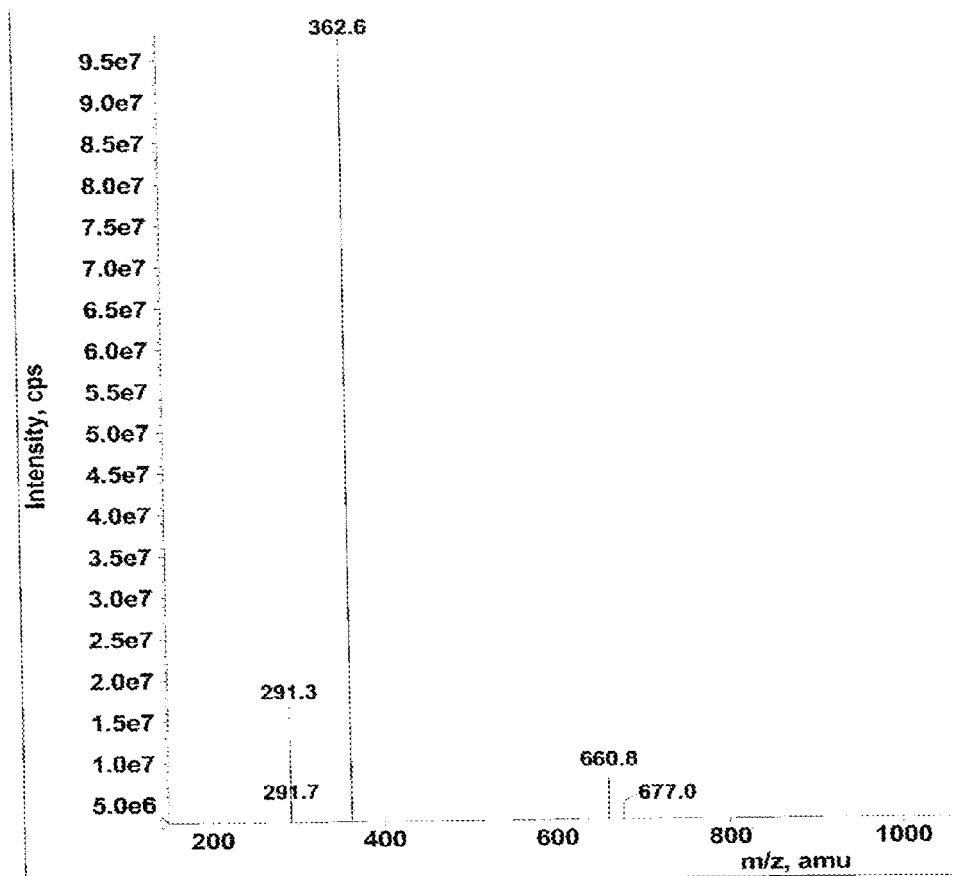
Figure 5: ESI/MS spectra of the $N$-(6-(bis(4-methoxyphenyl)(phenyl)methoxy)-5-(hydroxymethyl)hexyl)-5-(1,2-dithiolan-3-yl)pentanamide compound 7. MS $m/z$ $C_{36}H_{47}NO_5S_2$+Na ([M + Na]$^+$ 660.29, calcd 660.8).

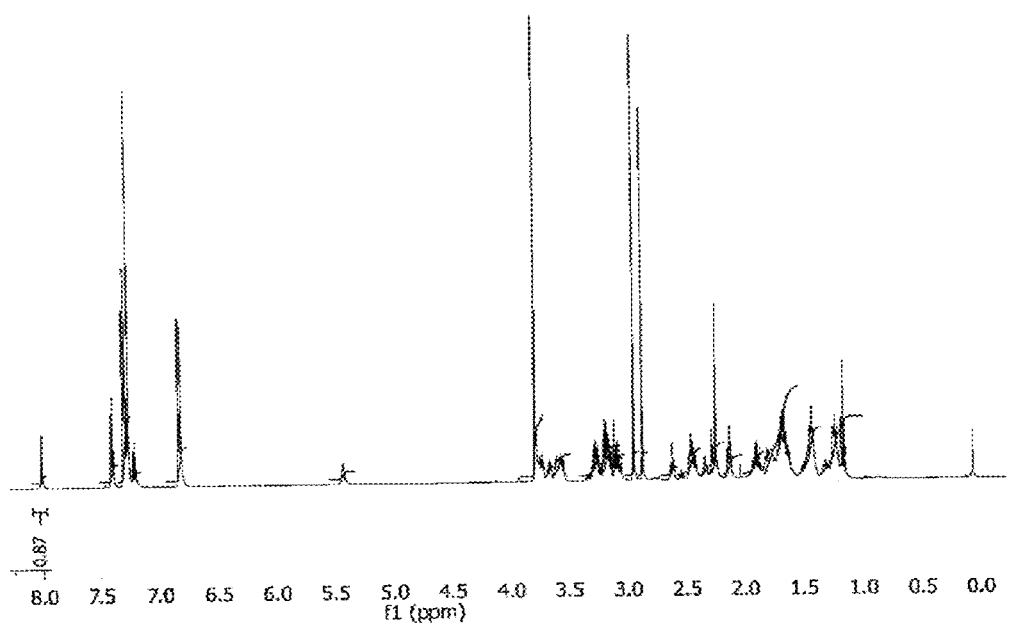
Figure 6: $^1$H NMR of N-(6-(bis(4-methoxyphenyl)(phenyl)methoxy)-5-(hydroxymethyl)hexyl)-5-(1,2-dithiolan-3-yl)pentanamide compound 7.

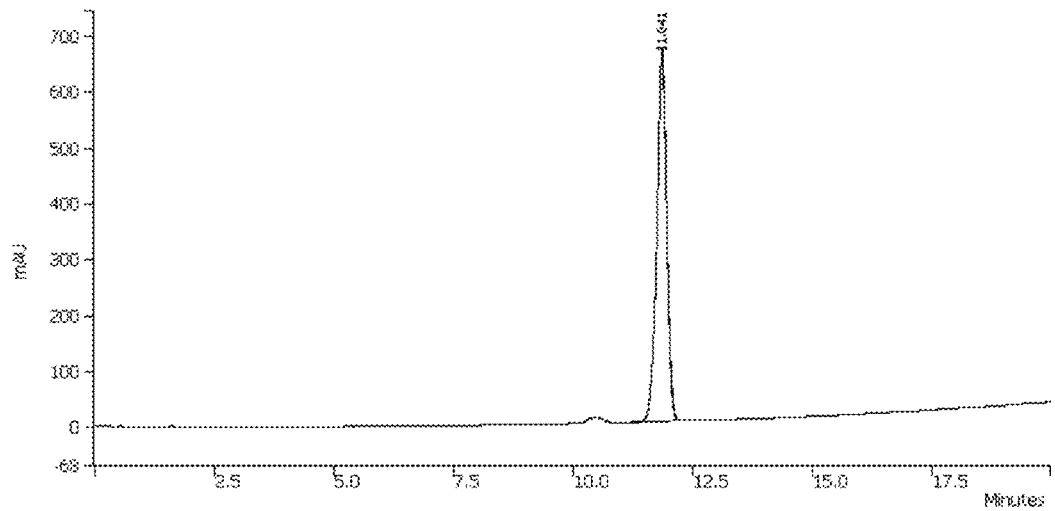

Figure 7: HPLC purity analysis of the 6-(5-(1,2-dithiolan-3-yl)pentanamido)-2-((bis(4-methoxyphenyl)(phenyl)methoxy)methyl)hexyl 2-cyanoethyl diisopropylphosphoramidite compound 1.

| Peak No | Peak Name | Ret Time (min) | Peak Area (counts) | Result (Area %) |
|---|---|---|---|---|
| 1 | | 2.089 | 52497 | 0.05 |
| 2 | | 2.709 | 42307 | 0.04 |
| 3 | | 3.570 | 83479 | 0.08 |
| 4 | | 5.253 | 32243 | 0.03 |
| 5 | | 6.754 | 99220 | 0.10 |
| 6 | | 6.924 | 68194 | 0.07 |
| 7 | | 10.422 | 2381236 | 2.31 |
| 8 | | 11.842 | 95979560 | 97.21 |
| 9 | | 13.796 | 52235 | 0.05 |
| 10 | | 14.385 | 44438 | 0.05 |
| | Totals | | 98735408 | 99.99 |

Figure 8: HPLC table peaks of the 6-(5-(1,2-dithiolan-3-yl)pentanamido)-2-((bis(4-methoxyphenyl)(phenyl)methoxy)methyl)hexyl 2-cyanoethyl diisopropylphosphoramidite compound 1.

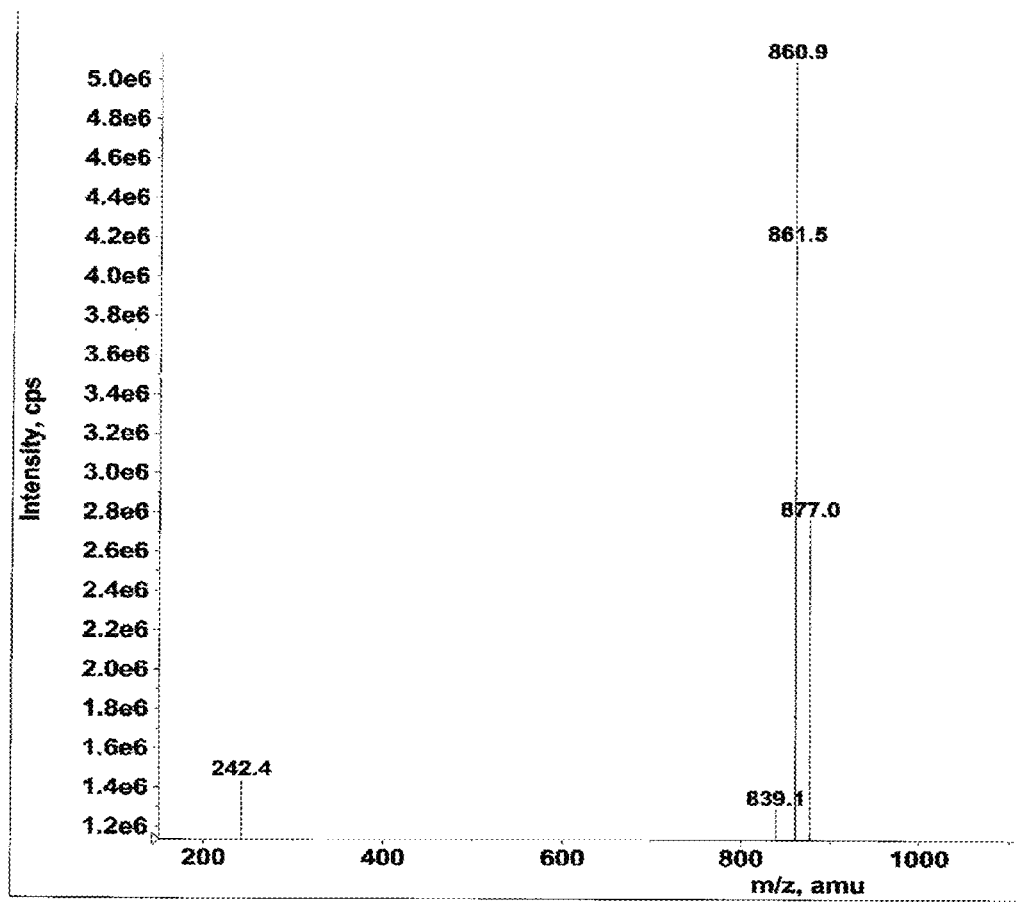
Figure 9: ESI/MS spectra of 6-(5-(1,2-dithiolan-3-yl)pentanamido)-2-((bis(4-methoxyphenyl)(phenyl)methoxy)methyl)hexyl 2-cyanoethyl diisopropylphosphoramidite compound 1. MS $m/z$ $C_{45}H_{64}N_3O_6PS_2 \cdot Na$ ([M + Na]$^+$ 860.40, calcd 860.90).

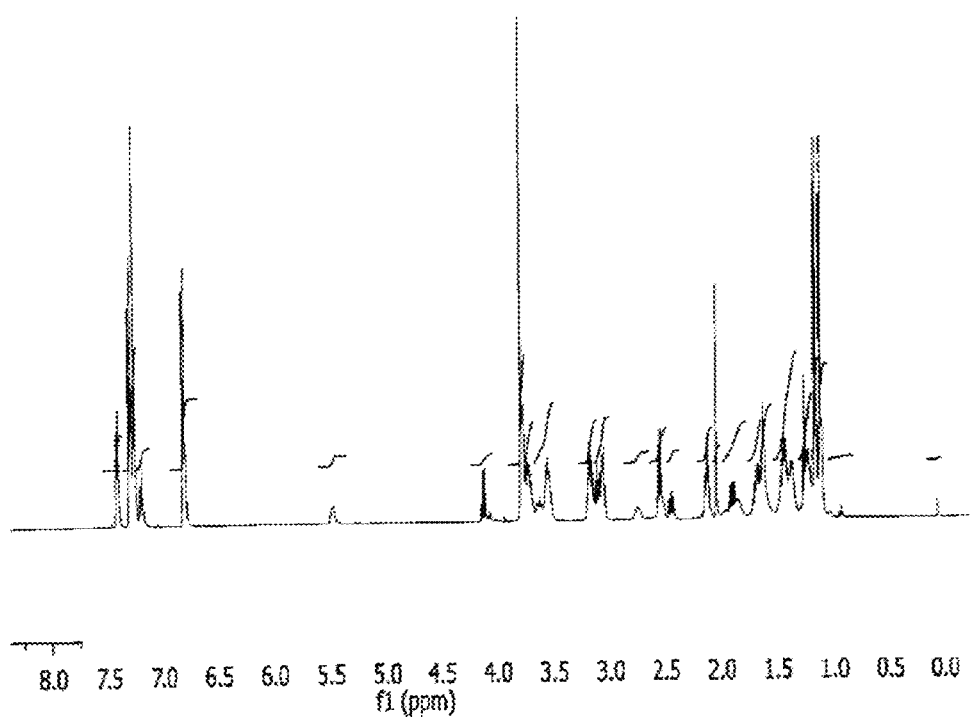
Figure 10: ¹H NMR of 6-(5-(1,2-dithiolan-3-yl)pentanamido)-2-((bis(4-methoxyphenyl)(phenyl)methoxy)methyl)hexyl 2-cyanoethyl diisopropylphosphoramidite compound 1.

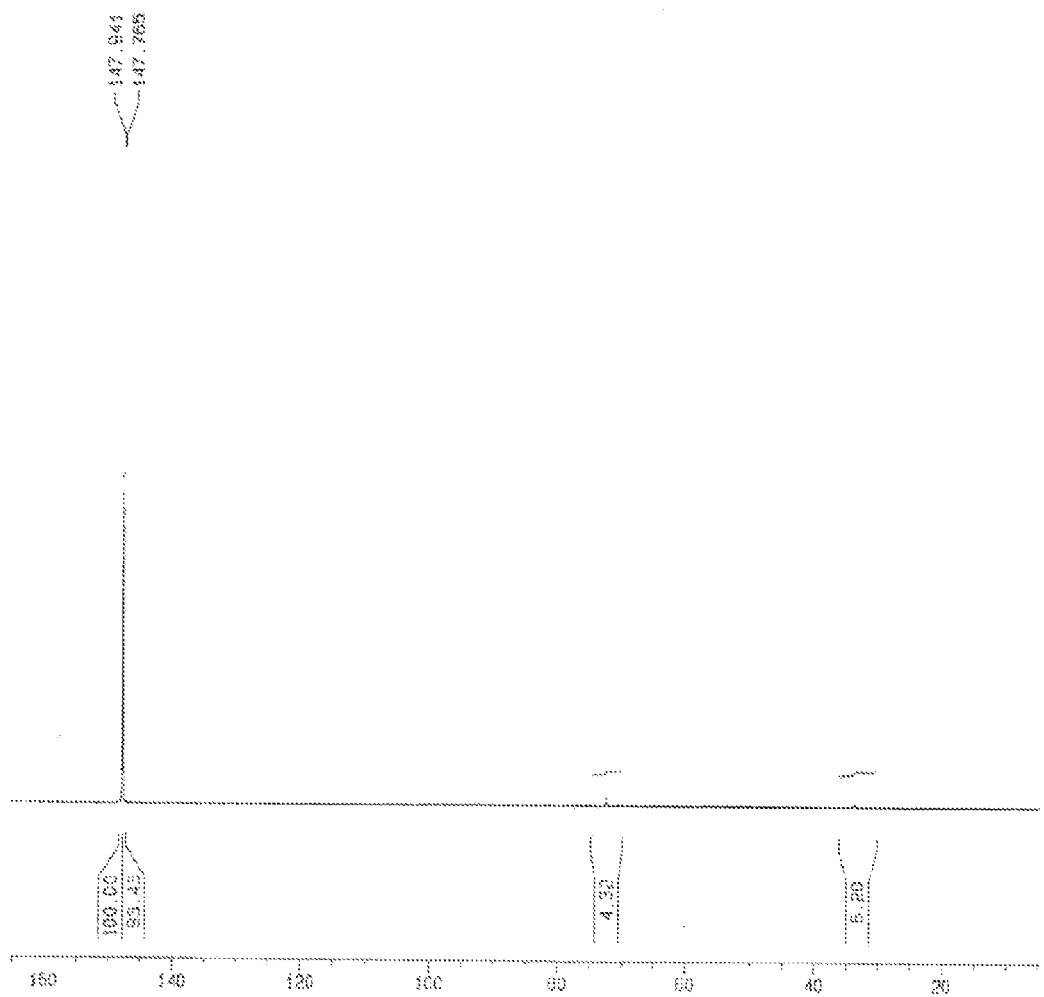
Figure 11: ³¹P NMR of 6-(5-(1,2-dithiolan-3-yl)pentanamido)-2-((bis(4-methoxyphenyl)(phenyl)methoxy)methyl)hexyl 2-cyanoethyl diisopropylphosphoramidite compound 1.

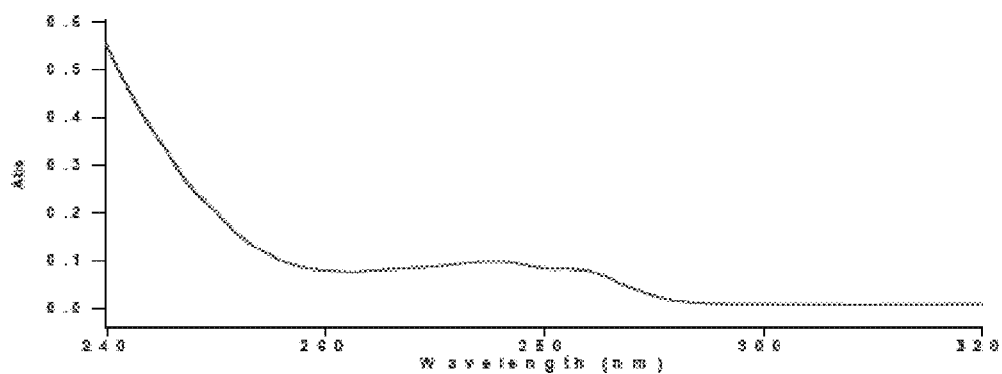
Figure 12: UV absorption spectra of 6-(5-(1,2-dithiolan-3-yl)pentanamido)-2-((bis(4-methoxyphenyl)(phenyl)methoxy)methyl)hexyl 2-cyanoethyl diisopropylphosphoramidite compound 1.

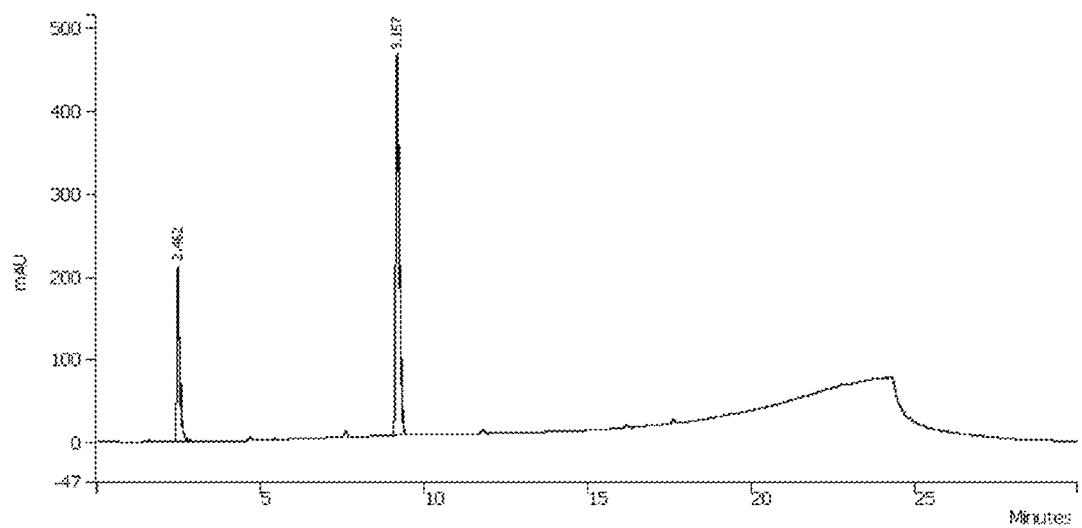

Figure 13: HPLC purity analysis of the 4-(6-(5-(1,2-dithiolan-3-yl)pentanamido)-2-((bis(4-methoxyphenyl)(phenyl)methoxy)methyl)hexyloxy)-4-oxobutanoate compound 8. peak with retention time of 2.46 min is pyridine and 9.15 min is the compound 8.

| Peak No | Peak Name | Ret Time (min) | Peak Area (counts) | Result (Area %) |
|---|---|---|---|---|
| 1 | | 2.462 | 12470740 | 25.40 |
| 2 | | 4.679 | 233999 | 0.48 |
| 3 | | 5.396 | 57634 | 0.12 |
| 4 | | 7.577 | 468816 | 0.95 |
| 5 | | 9.158 | 34963268 | 71.20 |
| 6 | | 9.612 | 24752 | 0.05 |
| 7 | | 10.112 | 30471 | 0.06 |
| 8 | | 10.417 | 64296 | 0.13 |
| 9 | | 11.788 | 278547 | 0.57 |
| 10 | | 16.194 | 218999 | 0.45 |
| 11 | | 17.607 | 291449 | 0.59 |
| | Totals | | 49101972 | 100.00 |

Figure 14: HPLC table peaks of the 4-(6-(5-(1,2-dithiolan-3-yl)pentanamido)-2-((bis(4-methoxyphenyl)(phenyl)methoxy)methyl)hexyloxy)-4-oxobutanoate compound 8.

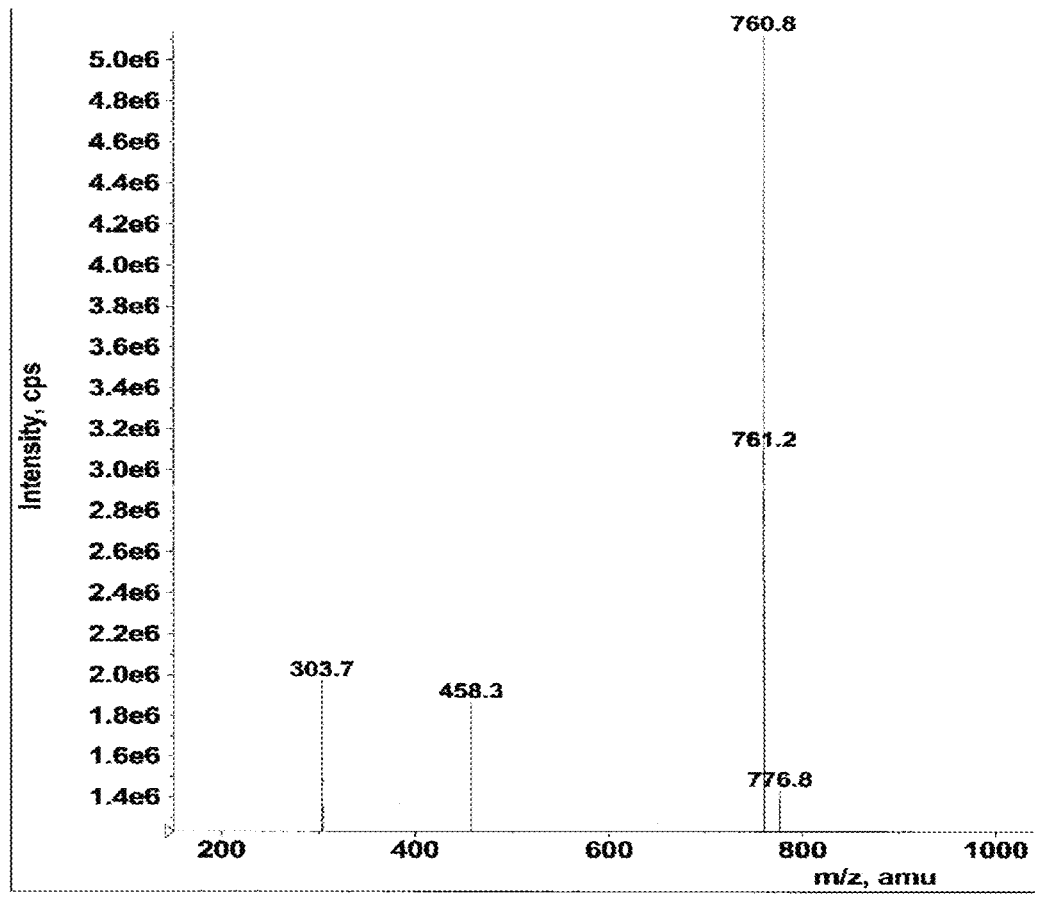
Figure 15: ESI/MS spectra of 4-(6-(5-(1,2-dithiolan-3-yl)pentanamido)-2-((bis(4-methoxyphenyl)(phenyl)methoxy)methyl)hexyloxy)-4-oxobutanoate compound 8. MS m/z $C_{40}H_{50}NO_8S_2 \cdot Na$ ([M + Na]$^+$ 759.9, calcd 760.8)

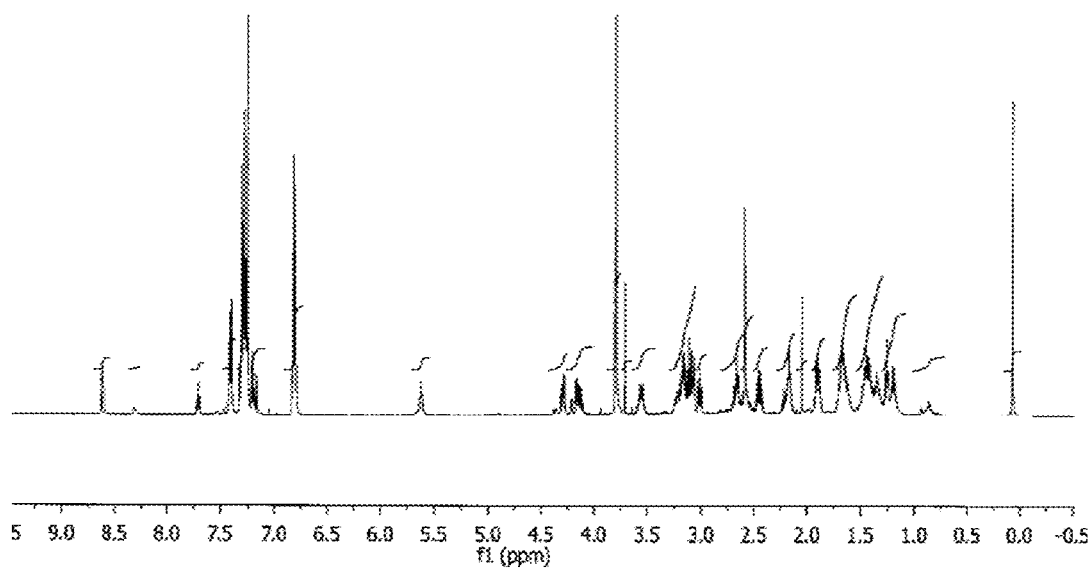
Figure 16: ¹H NMR of -(6-(5-(1,2-dithiolan-3-yl)pentanamido)-2-((bis(4-methoxyphenyl)(phenyl)methoxy)methyl)hexyloxy)-4-oxobutanoate compound 8.

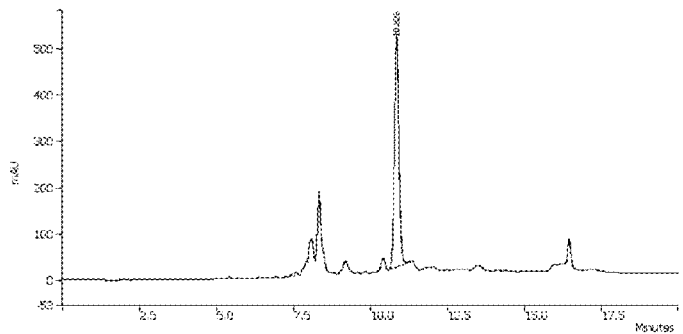
Figure 17a
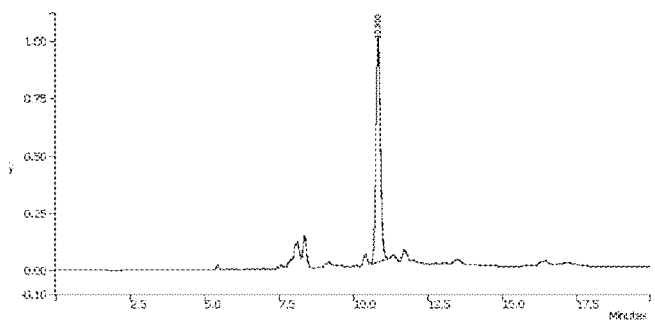
Figure 17b
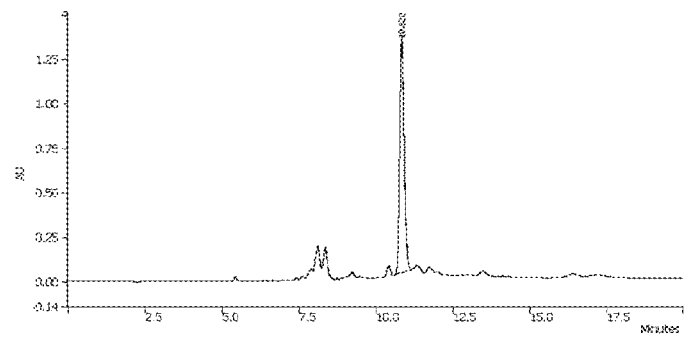
Figure 17c: Purity analysis of the crude oligonucleotide 5'-XAC TTG GCT CCA AGT CAC CGT T-3' (SEQ. ID No. 1), where is X is dithiolane modification, after subjecting to three different deprotection conditions *viz* a) AMA reagent, 30 min at room temperature then for 1 h at 50 °C; b) aqueous NH$_3$ at 37 °C for 24 h; and c) aqueous NH$_3$ at 50 C for 16 h.

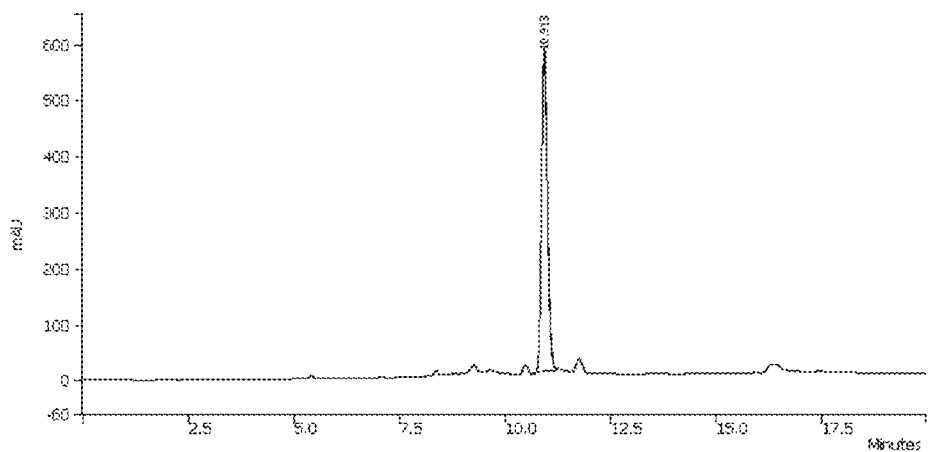

Figure 18: Purity analysis of the pure oligonucleotide ON1 5'-<u>X</u>CT TGG CTC CAA GTC ACC GTT-3' (SEQ. ID No. 1), where is X is dithiolane modification, after purification of crude oligo by HPLC on Source 15Q ion-exchange column (1.0 cm X 25 cm).

| Peak No | Peak Name | Ret Time (min) | Peak Area (counts) | Result (Area %) |
|---|---|---|---|---|
| 1 | | 3.421 | 16363 | 0.02 |
| 2 | | 5.405 | 353117 | 0.52 |
| 3 | | 8.143 | 49453 | 0.07 |
| 4 | | 8.343 | 579951 | 0.85 |
| 5 | | 9.236 | 1725784 | 2.54 |
| 6 | | 9.638 | 1505675 | 2.21 |
| 7 | | 10.087 | 117889 | 0.17 |
| 8 | | 10.468 | 1429617 | 2.10 |
| 9 | | 10.913 | 59284972 | 87.21 |
| 10 | | 11.738 | 2628205 | 3.87 |
| 11 | | 12.403 | 287886 | 0.42 |
| | Totals | | 67978912 | 99.98 |

Figure 19: HPLC Table peaks of pure oligonucleotide 5'-<u>X</u>AC TTG GCT CCA AGT CAC CGT T-3' (SEQ. ID No. 1), where is X is dithiolane modification.

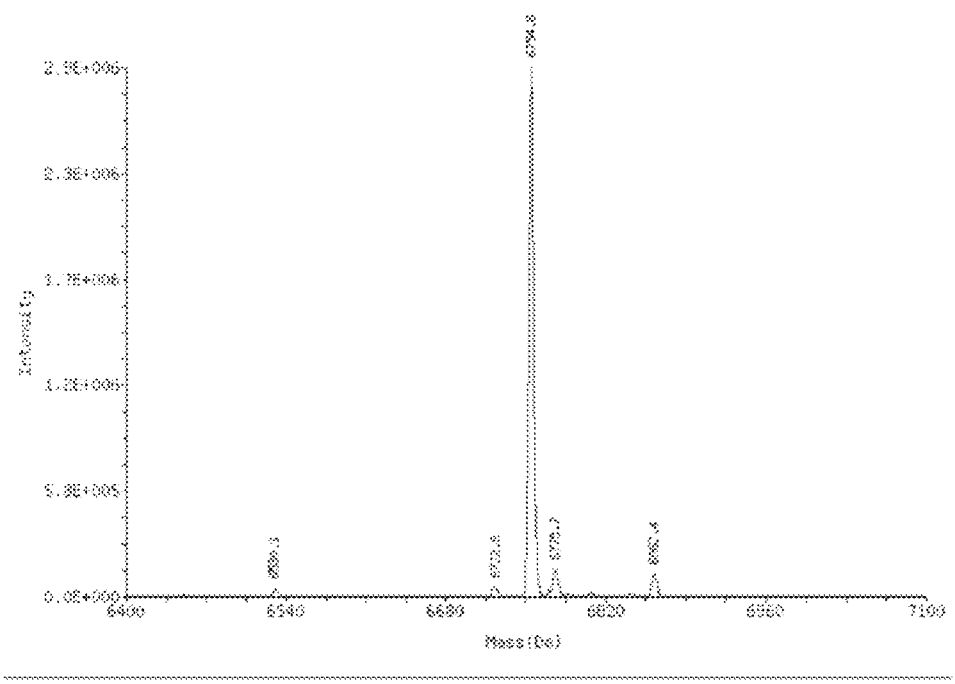
Figure 20: ESI-MS of the pure ON1 5'-XAC TTG GCT CCA AGT CAC CGT T-3' (SEQ. ID No. 1), where is X is dithiolane modification. Found *m/z* [M-H]⁻ 6754 and Calc *m/z* [M-H]⁻ 6754.

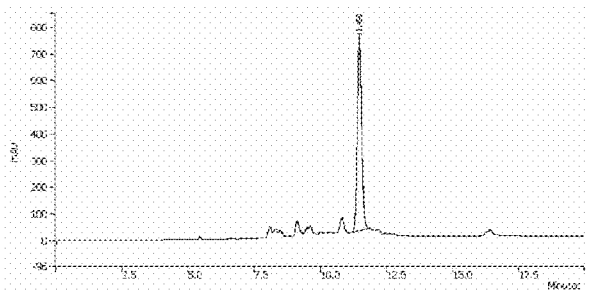
Figure 21a:
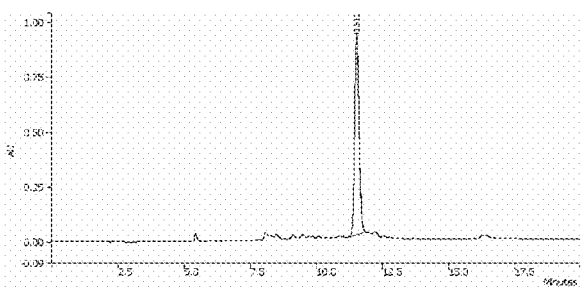
Figure 21b:
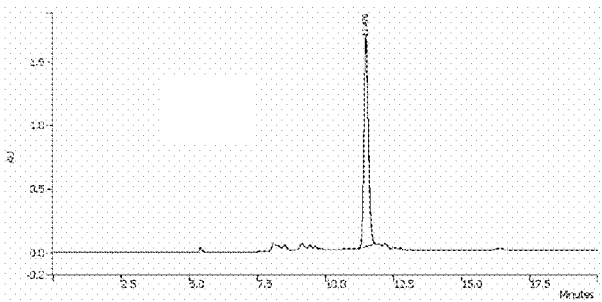
Figure 21 c: Purity analysis of the crude oligonucleotide ON2 5'ACT TGG CTC CAX AGT CAC CGT T -3' (SEQ. ID No. 2), where is X is dithiolane modification after subjecting to three different deprotection conditions *viz.*, a) AMA reagent, 30 min at room temperature then for 1 h at 50 °C; b) aqueous NH$_3$ at 37 °C for 24 h; and c) aqueous NH$_3$ at 50 C for 16 h.

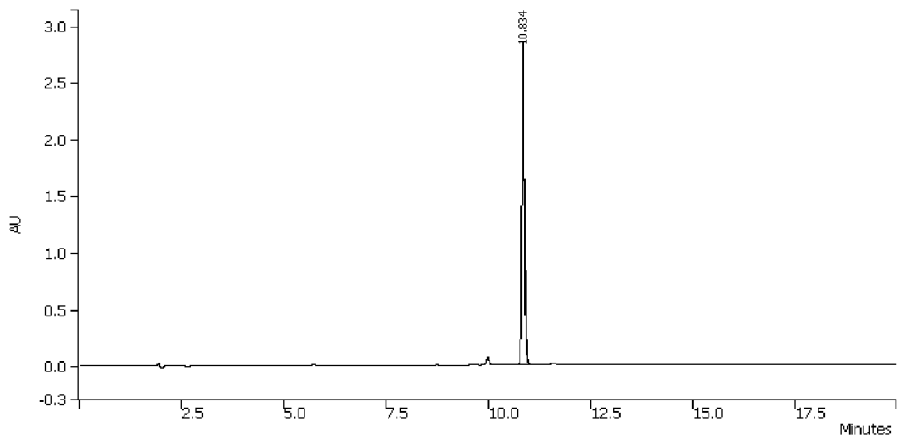

Figure 22: Purity analysis of the pure oligonucleotide ON2 5'ACT TGG CTC CAX AGT CAC CGT T-3' (SEQ. ID No. 2), where is X is dithiolane modification, after purification of crude oligo by HPLC on Source 15Q ion-exchange column (1.0 cm X 25 cm).

| Peak No | Peak Name | Ret Time (min) | Peak Area (counts) | Result (Area %) |
|---|---|---|---|---|
| 1 |  | 2.731 | 105970 | 0.08 |
| 2 |  | 3.253 | 208264 | 0.16 |
| 3 |  | 3.727 | 339915 | 0.27 |
| 4 |  | 5.098 | 245115 | 0.19 |
| 5 |  | 5.719 | 685418 | 0.54 |
| 6 |  | 7.877 | 40295 | 0.03 |
| 7 |  | 8.263 | 37053 | 0.03 |
| 8 |  | 8.736 | 136121 | 0.11 |
| 9 |  | 8.959 | 53633 | 0.04 |
| 10 |  | 9.304 | 61610 | 0.05 |
| 11 |  | 9.579 | 254442 | 0.20 |
| 12 |  | 9.963 | 3239883 | 2.55 |
| 13 |  | 10.282 | 36532 | 0.03 |
| 14 |  | 10.834 | 118878736 | 93.56 |
| 15 |  | 11.559 | 1633505 | 1.29 |
| 16 |  | 11.707 | 745432 | 0.59 |
| 17 |  | 14.242 | 195544 | 0.15 |
| 18 |  | 14.880 | 47815 | 0.04 |
| 19 |  | 15.305 | 46514 | 0.04 |
| 20 |  | 15.575 | 65149 | 0.05 |
|  | Totals |  | 127056944 | 100.00 |

Figure 23: HPLC table peaks of the pure oligonucleotide ON2 5'ACT TGG CTC CAX AGT CAC CGT T' (SEQ. ID No. 2), where is X is dithiolane modification.

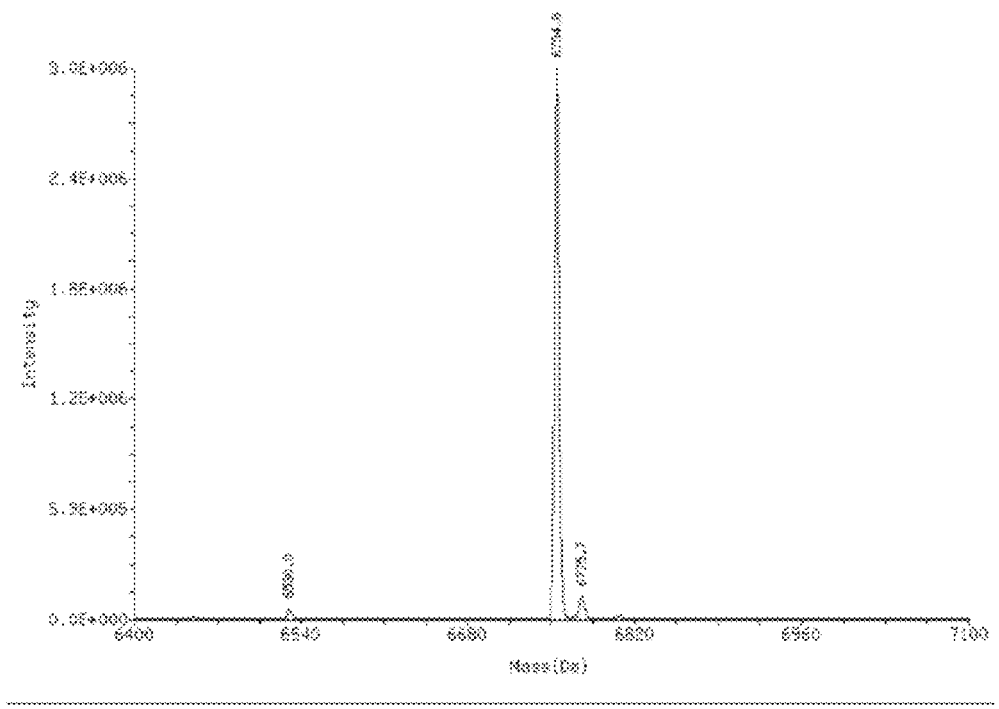
Figure 24: ESI-MS of the pure ON2 5'ACT TGG CTC CAX AGT CAC CGT T (SEQ. ID No. 2), where is X is dithiolane modification, Found *m/z* [M-H]⁻ 6754 and Calc *m/z* [M-H]⁻ 6754.

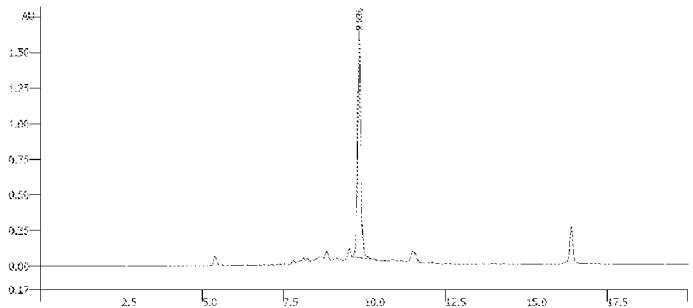
Figure 25a)
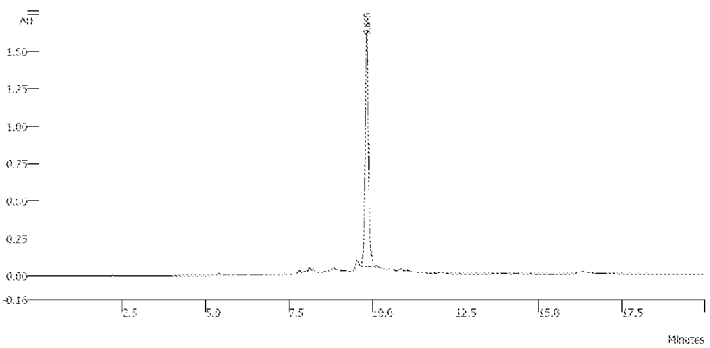
Figure 25b)
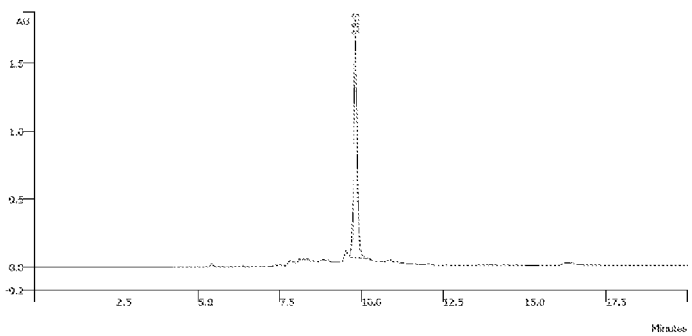
Figure 25c: Purity analysis of the crude oligonucleotide ON3 5'-ACT TGG CTC CAA GTC ACC GT<u>X</u>-3' (SEQ. ID No. 3), where is <u>X</u> is dithiolane modification, after subjecting to three different deprotection conditions *viz.* a) AMA reagent, 30 min at room temperature then for 1 h at 50 °C; b) aqueous $NH_3$ at 37 °C for 24 h; and c) aqueous $NH_3$ at 50 C for 16 h.

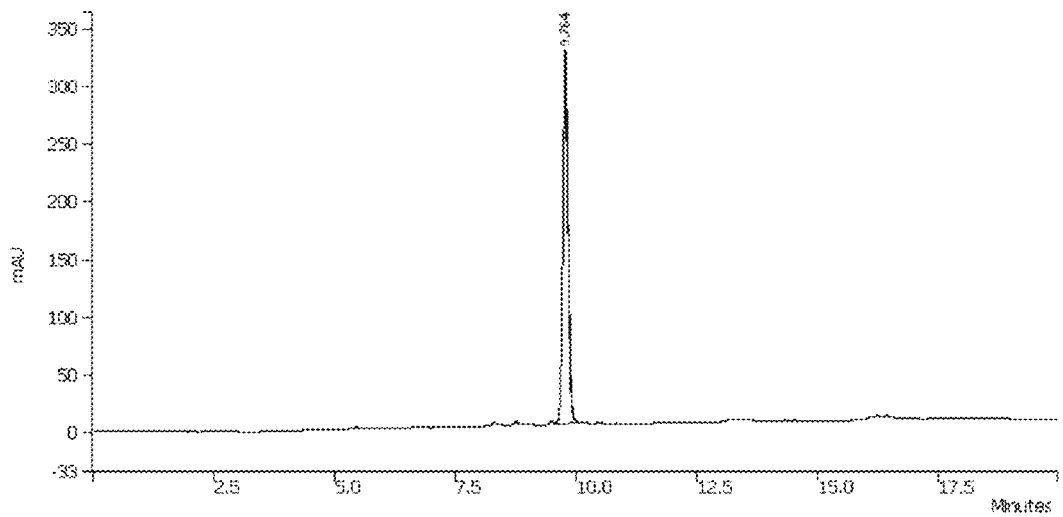

Figure 26: Purity analysis of the pure oligonucleotide ON3 5'-ACT TGG CTC CAA GTC ACC GT<u>X</u>-3' (SEQ. ID No. 3), where is <u>X</u> is dithiolane modification, after purification of crude oligo by HPLC on Source 15Q ion-exchange column (1.0 cm X 25 cm).

| Peak No | Peak Name | Ret Time (min) | Peak Area (counts) | Result (Area %) |
|---|---|---|---|---|
| 1 | | 5.437 | 100166 | 0.40 |
| 2 | | 8.283 | 159177 | 0.64 |
| 3 | | 8.747 | 148599 | 0.59 |
| 4 | | 9.467 | 206498 | 0.83 |
| 5 | | 9.764 | 24274532 | 97.20 |
| 6 | | 10.163 | 30570 | 0.12 |
| 7 | | 10.816 | 55198 | 0.22 |
| Totals | | | 24974740 | 100.00 |

Figure 27: HPLC Table peaks the pure oligonucleotide ON3 5'-ACT TGG CTC CAA GTC ACC GTX-3' (SEQ. ID No. 3), where is X is dithiolane modification.

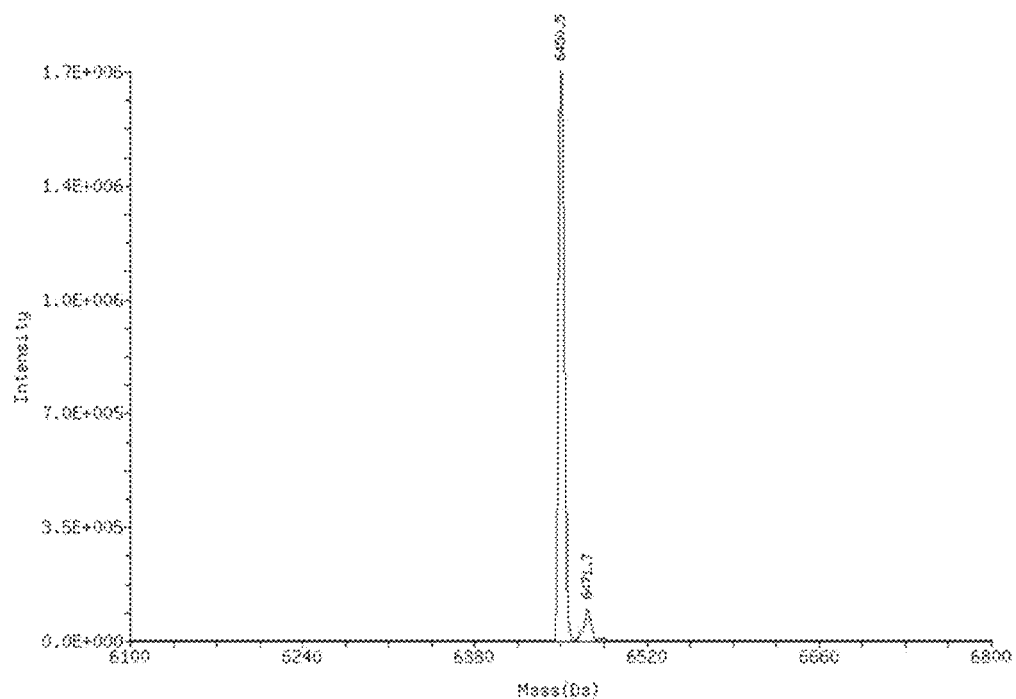
Figure 28: ESI-MS of the pure ON3 5'-ACT TGG CTC CAA GTC ACC GT<u>X</u> (SEQ. ID No. 3), Found *m/z* [M-H]⁻ 6450 and Calc *m/z* [M-H]⁻ 6450.

DITHIOLANE BASED THIOL MODIFIER FOR LABELING AND STRONGER IMMOBILIZATION OF BIO-MOLECULES ON SOLID SURFACES

FIELD OF THE INVENTION

This invention is related to nucleic acid chemistry and describes novel 1,2-dithiolane posphoramidites (1, Chart 1) and corresponding solid supports (2, Chart 1). The symmetrical branching nature of the spacer in the linker arm of dithiolane allows for clean oligo synthesis, where cleavage of the linker arm and thereby of loss of oligo chain is prevented. These derivatives are useful for introduction of multiple reactive thiol groups for labeling and for stronger immobilization of bio-molecules such as oligonucleotides and peptides on solid surfaces such as gold, silver and quantum dots. Pairs of oligonucleotide-gold nanoparticle conjugates serve as unique probes for recognizing specific sequences in DNA segments, as building blocks for assembling novel structures, bio diagnostics and nano technology based therapeutics.

BACKGROUND OF THE INVENTION

In the recent years, development of nanometer sized structures has received much attention for various molecular biological applications. Gold is probably the most suited element because it exhibits a high chemical stability (noble metal), is characterized by its ability to strongly absorb the visible light at definite wavelengths and is intrinsically not toxic. The thiol (R—SH) modified oligonucleotides serve as attractive tools with a vast number of potential applications in the field of nucleic acid chemistry such as it enables covalent attachment of variety of ligands that contain a) α,β-unsaturated ketone; b) maleimide c) other Michael acceptor groups or d) cysteines in proteins to make disulfide bonds. In addition to this, thiol has a strong specific interaction with gold surface to form reversible covalent bond with gold.

The reactive thiol group can be introduced into oligonucleotides by incorporating sulfide modified phosphoramidite monomers during oligonucleotide synthesis. Generally, two different types of sulfide modified monomers viz disulfide stratagy [Jones, D. S., Hachmann, J. P., Conrad, M. J., Coutts, S., Livingston, D. A. U.S. Pat. No. 5,391,785, 1995] or S-trityl protection [Connolly, B. A.; Rider, P. *Nucleic Acids Res.* 1985 13, 4485] are very popular to achieve this. Reactive thiol group from the disulfide is generated by treating oligo with reducing agent such as dithiothreitol (DTT). Whereas, in the other S-trityl strategy, it is generated by cleaving trityl group by silver nitrate. However, this strategy has clear disadvantage of elaborate cleavage process of trityl group with the silver nitrate, which results in relatively poor yields of the final oligonucleotide. Hence, disulfide modified phosphoramidites serve as superior probes for generating thiol groups. The most popular disulfide probes are with the general formula DMT-O—R—S—S—R—O—P(CE)(NiPr$_2$), where R being C3 or C6 (3, chart 1) spacer arm [Jones, D. S., Hachmann, J. P., Conrad, M. J., Coutts, S., Livingston, D. A. U.S. Pat. No. 5,391,785, 1995]. The synthesis of phosphoramidites 3 (where n=6, Chart 1) and supports 4 (where n=6, Chart 1) with C6 arm is simple and high yielding [Jones, D. S., Hachmann, J. P., Conrad, M. J., Coutts, S., Livingston, D. A. U.S. Pat. No. 5,391,785, 1995]. However, synthesis of C3 disulfide phosphoramidite compound 3 (Chart 1, where n=3) has recently been reported very briefly by Yosuke Taniguchia et. al. [Taniguchi, Nitta, A., Park, S. M., Kohara, A., Uzu, T., Sasaki, S. *Bioorg. Med. Chem.* 2010, 18, 8614]

The reported synthetic protocol was not reproducible in generating the target compound 3 (Chart 1, where n=3) in our hands and purification procedure was not reported. We therefore carried out detailed investigation to develop a new synthetic and purification method that gives phosphoramidite 3 (Chart 1, where n=3) in a high purity for commercial, research and development. Our optimized synthetic protocol is reproducible, suitable for multi gram scale and yields target phosphoramidite 3 (Chart 1, where n=3) in high purity by $^{31}$P NMR (>94%). [Srivastava, S. C.; Thatikonda, S. K.; Srivastav, S. K. Shukla, P. U.S. Patent Application No. 2012/000103, 2012]

Chart 1: Chemical structures of target dithiolane phosphoramidites 1, solid supports 2 and currently used most popular acyclic disulfides with C6 and C3 spacer phosphoramidites 3 and their solid supports 4.

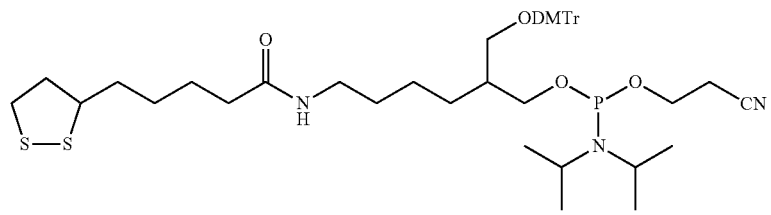

1

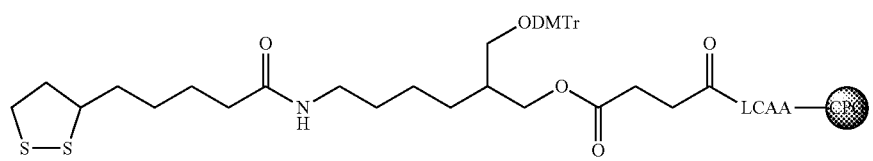

2

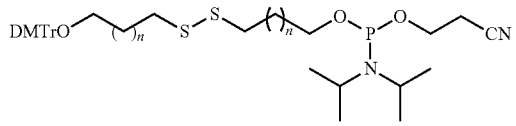

Where n = 1 or 4

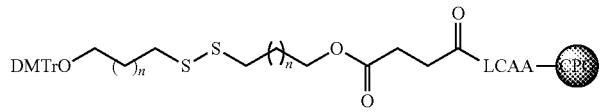

Where n = 1 or 4

Nuzzo and Allara have discovered that reactive thiol group adsorb on gold surface and forms ordered mono layers. [Nuzzo, R. G., Allara, D. L. Jour. Am. Chem. Soc. 1983, 105, 4481]. After this, oligonucleotides with thiol group are very much used to generate self assembled monolayers (SAMs) on the gold surfaces. Although different molecules can be immobilized (silanes, carboxylic acids, pyridines, sulphites and thiols) on different surfaces (gold, silver, platinum, copper, mercury and glass), chemisorption of thiols on gold is a common and simple procedure to immobilize probes on a surface. DNA functionalized gold nanoparticles have since become widely used building blocks in key nucleic acid based assembly strategies and serve as unique probes for recognizing specific sequences in DNA segments [Storhoff, J. J., Elghanian, R., Mucic, R. C., Mirkin, C. A., and Letsinger, R. L. J. Am. Chem. Soc. 1998 120, 1959] as a building blocks for assembling novel structures and materials [Mucic, R. C., Storhoff, J. J., Mirkin, C. A., Letsinger, R. L. J. Am. Chem. Soc. 1998 120, 12674] and bio diagnostics and nano technology based therapeutics [Merkins, C. A., Letsinger, R. L., Mucic, R. C., Storhoff, J. J. Nature, 1996, 382, 607; Hurst, S. J., Hill, H. D., Mirkin, C. A. J. Am. Chem. Soc. 2008, 130, 12192]. It has been proven that formation of these monolayers is influenced by several factors such as temperature, solvent, buffer concentration, chain length of the adsorbate, cleanliness of the substrate, rate of reaction with the surface and the reversibility of adsorption of the components of the monolayer. These applications depend on the reversible association of gold and sulfur bond between the attached oligonucleotide and nano particle.

The oligonucleotides attached with single thiol group are unstable during the washing steps and formation of stable attachment of oligonucleotides is very important property for its success in applications such as for DNA chip technology. The covalent bond between gold and sulfur is in the order of magnitude from 30 to 40 Kcal/mol, which is relatively weak in order to anchor a biopolymer onto a surface. [Dubois L. H., Zegarski B. R., Nuzzo R. G. Proc. Natl. Acad. Sci. USA 1987 84 4739; Liepold, P., Kratzmüller, T., Persike, N., Bandilla, M., Hinz, M., Wieder, H., Hillebrandt, H., Ferrer, E., Hartwich, G. Anal Bioanal Chem, 2008, 391, 1759-1772]. It's been reported that oligonucleotides that are conjugated with mono functional thiol group are slowly lost at higher temperatures and also in the presence of high salt concentration buffers [Li, Z., Jin, R., Mirkin, C. A., Letsinger, R. L. Nucleic Acids Res. 2002, 30, 1558]. The stability studies by Letsinger et. al. on SAMs of oligonucleotides that are conjugated to gold surface by mono thiol group revealed that these are completely displaced by treating with the buffers containing DTT [Letsinger, R. L., Elghanian, R., Viswanadham, G., Mirkin, C. A. Bioconj. Chem. 2000, 11, 289]. This feature limits applications of these probes in solutions containing thiols such as a PCR solution that has DTT as a stabilizer for the polymerase enzyme.

So there is strong need to develop novel disulfide compounds that are capable of forming stable SAMs of oligonucleotides for wider biological applications. One can anticipate that stability of mono layers could be increased by multiple numbers of gold-sulfur bonds per oligonucleotides. There have been few reports [Letsinger, R. L., Elghanian, R., Viswanadham, G., Mirkin, C. A. Bioconj. Chem. 2000, 11, 289-291; Hartwich, G., Frischmann, P., Ferrer, E., U.S. Pat. No. 7,601,848, 2002; Seliger, H., Prokein, T. U.S. Patent No 2005/0059728, 2004] that has introduced novel thiol modifiers which can generate multiple thiol groups per oligonucleotide. Its been proved that SAMs produced by these modifications are much more stable than corresponding SAMs generated by mono thiol modifier in buffers containing DTT [Letsinger, R. L., Elghanian, R., Viswanadham, G., Mirkin, C. A. Bioconj. Chem. 2000, 11, 289].

The task of the present invention is to make novel disulfide monomer that can introduce poly functional thiol groups for immobilization or labeling. Herein, we describe five membered disulfide (dithiolane) based anchoring group 1 (Chart 1) for the introduction of one two thiol groups. This dithiolane modification is simple to synthesize, is broadly useful, and can potentially afford gold-oligonucleotide conjugates that exhibit greater stability. Previously, similar dithiolane based phosphoramidites and supports have been reported [Seliger, H., Prokein, T. U.S. Patent No 2005/0059728, 2004] for the synthesis of dithiolane probes. However, even though they claimed with longer spacer arm, reported synthesis was with shorter spacer arm. The successful attachment of oligonucleotides onto gold surface ideally requires relatively longer spacer arm. The other important issue with the previously reported dithiolane phosphoramidites is that, spacer arm is asymmetric branching chain with a secondary hydroxyl group carrying DMT group for oligo chain synthesis. Close proximity of hydroxyl group to the phosphodiester bond might result in nucleophilic attack, which further leads to chain cleavage of oligonucleotide strand. Similar side reaction leading to nucleophilic attack and subsequent chain cleavage of synthetic RNA is also very likely. Thus the quality of the dithiolane oligonucleotides and probes can be compromised. If multiple dithiolane moieties are attached into a defined sequence DNA or RNA, multiple scissions of oligonucleotides is possible and serious compromise of DNA or RNA is possible. To address these issues, we have planned a new probe design that has longer spacer arm.

We have designed a symmetrical linker such that free hydroxyl group will be generated at one carbon away from the phosphodiester group at 3' or 5' end of oligonucleotides. Symmetrical branching type of linker, as it placed away from the phosphodiester, avoids chain cleavage possibilities. With these improvements, we strongly believe that our probes are designed to be ideally suited to application in high quality probes consisting of dithiolane moieties.

REFERENCES

1) Connolly, B. A., Rider, P. *Nucleic Acids Res.* 1985 13, 4485
2) Dubois L. H., Zegarski B. R., Nuzzo R. G. *Proc. Nat. Acad. Sci. USA* 1987 84 4739-4742.
3) Elghanian, R., Storhoff, J. J., Mucic, R. C., Letsinger, R. L., Mirkin, C. A. 1997 *Science* 277, 1078-1081. Gottlieb, H. E., Kotlyar, V., Nudelman, A. *J. Org. Chem.* 1997, 62, 7512-7515.
4) Hartwich, G., Frischmann, P., Ferrer, E., U.S. Pat. No. 7,601,848, filed Dec. 21, 2002.
5) Hurst, S. J., Hill, H. D., Mirkin, C. A. *J. Am. Chem. Soc.* 2008, 130, 12192.
6) Jones, D. S., Hachmann, J. P., Conrad, M. J., Coutts, S., Livingston, D. A. U.S. Pat. No. 5,391,785, Date filed Feb. 21, 1995
7) Letsinger, R. L., Elghanian, R., Viswanadham, G., Mirkin, C. A. *Bioconj. Chem.* 2000, 11, 289-291.
8) Li, Z., Jin, R., Mirkin, C. A., Letsinger, R. L. *Nucleic Acids Res.* 2002, 30, 1558-62.
9) Liepold, P., Kratzmüller, T., Persike, N., Bandilla, M., Hinz, M., Wieder, H., Hillebrandt, H., Ferrer, E., Hartwich, G. *Anal Bioanal Chem,* 2008, 391, 1759-1772.
10) Merkins, C. A., Letsinger, R. L., Mucic, R. C., Storhoff, J. J. *Nature,* 1996, 382, 607.
11) Mucic, R. C., Storhoff, J. J., Mirkin, C. A., Letsinger, R. L. *J. Am. Chem. Soc.* 1998 120, 12674-12675.
12) Nelson, P. S., Kent, M., Muthini, S. *Nucleic Acids Res.* 1992 20, 6253-6259.
13) Nuzzo, R. G., Allara, D. L. *Jour. Am. Chem. Soc.* 1983, 105, 4481.
14) Seliger, H., Prokein, T. U.S. Patent No 2005/0059728 A1, filed Aug. 26, 2004
15) Srivastava, S. C.; Thatikonda, S. K.; Srivastav, S. K. Shukla, P. U.S. Patent Application No. 2012/000103, 2012.
16) Storhoff, J. J., Elghanian, R., Mucic, R. C., Mirkin, C. A., and Letsinger, R. L. *J. Am. Chem. Soc.* 1998 120, 1959-1964.
17) Taniguchi, Nitta, A., Park, S. M., Kohara, A., Uzu, T., Sasaki, S. *Bioorg. Med. Chem.* 2010, 18, 8614.

SUMMARY OF THE INVENTION

The thiol modified oligonucleotides have vast number of applications in the field of nucleic acid chemistry such as it enables covalent attachment of a variety of ligands and also has an ability to form relatively stronger bond with gold surface. Hence, oligos with thiol groups chemisorb onto gold surface and generates self assembled mono layers (SAMs). DNA functionalized gold nanoparticles have become widely used building blocks in key nucleic acid based assembly strategies and serve as unique probes for recognizing specific sequences in DNA segments, as building blocks for assembling novel structures and materials, bio diagnostics and nano technology based therapeutics.

Even though thiol group forms relatively stronger bond with elemental gold (about 30-40 Kcal/mole), it gets displaced at higher temperature, in high salt concentration buffers and in presence other thiols. For many of applications with these conjugates strong binding of the oligonucleotides to the gold nano particles is required. However to circumvent displacement of thiol, a few cyclic disulfide modifiers that can introduce multiple thiol groups have been introduced in the priorart. Their stability studies revealed that these multi-thiol functionalized oligonucleotides form relatively more stable SAMs compared to the corresponding mono-thiol derivatives.

In the present application, we describe the design and efficient synthesis of cyclic dithiolane phosphoramidite derivative 1 (Chart 1) and corresponding dithiolane succinyl CPG supports 2 (Chart 1). The advantage of this cyclic disulfide monomer is that each incorporation introduces two thiol groups at any desired position of oligonucleotides. The present inventors have successfully made 20-mer oligonucleotide containing single dithiolane derivative at 3', and 21-mer oligonucleotides containing single dithiolane derivative at 5' or in the middle of the mixed base sequence. HPLC and ESI MS analysis of these oligonucleotides indicated satisfactory purity and the exact composition of these oligos, respectively.

BRIEF DESCRIPTION OF DRAWINGS

FIG. 1: HPLC purity analysis of the 6-amino-2-((bis(4-methoxyphenyl)(phenyl)methoxy) methyl)hexan-1-ol compound 6. Analytical purity of compounds was checked using a Varian Prostar HPLC equipped with ChromSep SS column (4.6×250 mm) and ChromSep Guard-Column OmniSpher 5 C18. Mobile phase: A 0.1M Triethylammonium acetate (TEAA); B is $CH_3CN$. Analysis was performed with the linear gradient of increase of B from 45-98% in 20 min. Peaks were detected by UV absorption at 254 nm.

FIG. 2: HPLC table peaks of the 6-amino-2-((bis(4-methoxyphenyl)(phenyl)methoxy) methyl)hexan-1-ol compound 6.

FIG. 3: HPLC purity analysis of the N-(6-(bis(4-methoxyphenyl)(phenyl)methoxy)-5-(hydroxymethyl)hexyl)-5-(1,2-dithiolan-3-yl)pentanamide compound 7. Analytical purity of compounds was checked using a Varian Prostar HPLC equipped with ChromSep SS column (4.6×250 mm) and ChromSep Guard-Column OmniSpher 5 C18. Mobile phase: A 0.1M Triethylammonium acetate (TEAA); B is $CH_3CN$. Analysis was performed with the linear gradient of increase of B from 45-98% in 20 min. Peaks were detected by UV absorption at 254 nm.

FIG. 4: HPLC table peaks of the N-(6-(bis(4-methoxyphenyl)(phenyl)methoxy)-5-(hydroxymethyl)hexyl)-5-(1,2-dithiolan-3-yl)pentanamide compound 7.

FIG. 5: ESI/MS spectra of the N-(6-(bis(4-methoxyphenyl)(phenyl)methoxy)-5-(hydroxymethyl)hexyl)-5-(1,2-dithiolan-3-yl)pentanamide compound 7. MS m/z C36H47NO5S2+Na ([M+Na]$^+$ 660.29, calcd 660.8). ESI/MS analysis was carried on Perkin Elmer PE-SCIEX API-150 mass spectrometer.

FIG. 6: $^1$H NMR N-(6-(bis(4-methoxyphenyl)(phenyl)methoxy)-5-(hydroxymethyl)hexyl)-5-(1,2-dithiolan-3-yl)pentanamide compound 7. $^1$H NMR was recorded on Bruker 500 MHz NMR spectrophotometer. Chemical shifts are calibrated with deuterated solvent $CDCl_3$ (δ 7.26 ppm).

FIG. 7: Purity analysis of the 6-(5-(1,2-dithiolan-3-yl)pentanamido)-2-((bis(4-methoxyphenyl)(phenyl)methoxy) methyl)hexyl 2-cyanoethyl diisopropylphosphoramidite compound 1. Analytical purity of compounds was checked using a Varian Prostar HPLC equipped with ChromSep SS column (4.6×250 mm) and ChromSep Guard-Column OmniSpher 5 C18. Mobile phase: A 0.1M Triethylammonium acetate (TEAA); B is $CH_3CN$. Analysis was performed with the linear gradient of increase of B from 80-100% in 20 min. Peaks were detected by UV absorption at 254 nm.

FIG. 8: HPLC table peaks of the 6-(5-(1,2-dithiolan-3-yl) pentanamido)-2-((bis(4-methoxyphenyl)(phenyl)methoxy) methyl)hexyl 2-cyanoethyl diisopropylphosphoramidite compound 1.

FIG. 9: ESI/MS spectra of the 6-(5-(1,2-dithiolan-3-yl) pentanamido)-2-((bis(4-methoxyphenyl)(phenyl)methoxy) methyl)hexyl 2-cyanoethyl diisopropylphosphoramidite compound 1. ESI/MS analysis was carried on Perkin Elmer PE-SCIEX API-150 mass spectrometer.

FIG. 10: $^1$H NMR of 6-(5-(1,2-dithiolan-3-yl)pentanamido)-2-((bis(4-methoxyphenyl)(phenyl)methoxy)methyl) hexyl 2-cyanoethyl diisopropylphosphoramidite compound 1. $^1$H NMR was recorded on Bruker 500 MHz NMR spectrophotometer. Chemical shifts are calibrated with deuterated solvent CDCl$_3$ (δ 7.26 ppm).

FIG. 11: $^{31}$P NMR spectra of 6-(5-(1,2-dithiolan-3-yl) pentanamido)-2-((bis(4-methoxyphenyl)(phenyl)methoxy) methyl)hexyl 2-cyanoethyl diisopropylphosphoramidite compound 1. $^{31}$P NMR was recorded on Bruker 202 MHz NMR spectrophotometer. Solvent used for NMR analysis was CDCl$_3$.

FIG. 12: UV absorption spectra of 6-(5-(1,2-dithiolan-3-yl)pentanamido)-2-((bis(4-methoxyphenyl)(phenyl) methoxy)methyl)hexyl2-cyano ethyl diisopropylphosphoramidite compound 1. UV absorption spectrum was recorded on Cary 50 Bio UV-Visible spectrophotometer in the range of 320 to 240 nm.

FIG. 13: Purity analysis of the 4-(6-(5-(1,2-dithiolan-3-yl)pentanamido)-2-((bis(4-methoxyphenyl)(phenyl) methoxy)methyl)hexyloxy)-4-oxobutanoate compound 8. Analytical purity of compounds was checked using a Varian Prostar HPLC equipped with ChromSep SS column (4.6× 250 mm) and ChromSep Guard-Column OmniSpher 5 C18. Mobile phase: A 0.1M Triethylammonium acetate (TEAA); B is CH$_3$CN. Analysis was performed with the linear gradient of increase of B from 45-98% in 20 min. Peaks were detected by UV absorption at 254 nm.

FIG. 14: HPLC table peaks of the 4-(6-(5-(1,2-dithiolan-3-yl)pentanamido)-2-((bis(4-methoxyphenyl)(phenyl) methoxy)methyl)hexyloxy)-4-oxobutanoate compound 8.

FIG. 15: ESI/MS spectra of the 4-(6-(5-(1,2-dithiolan-3-yl)pentanamido)-2-((bis(4-methoxyphenyl)(phenyl) methoxy)methyl)hexyloxy)-4-oxobutanoate compound 8. ESI/MS analysis was carried on Perkin Elmer PE-SCIEX API-150 mass spectrometer.

FIG. 16: $^1$H NMR of 4-(6-(5-(1,2-dithiolan-3-yl)pentanamido)-2-((bis(4-methoxyphenyl)(phenyl)methoxy)methyl) hexyloxy)-4-oxobutanoate compound 8. $^1$H NMR was recorded on Bruker 500 MHz NMR spectrophotometer. Chemical shifts are calibrated with deuterated solvent CDCl$_3$ (δ 7.26 ppm).

FIG. 17: Purity analysis of the crude oligonucleotide ON1 5'-XAC TTG GCT CCA AGT CAC CGT T-3' (Seq. ID No 1), where is X is dithiolane modification after subjecting to three different deprotection conditions a) AMA reagent, 30 min at room temperature then for 1 h at 50° C.; b) aqueous NH$_3$ at 37° C. for 24 h; and c) aqueous NH$_3$ at 50 C for 16. Analytical purity of compounds was checked using a Varian Prostar HPLC equipped with ChromSep SS column (4.6× 250 mm) and ChromSep Guard-Column OmniSpher 5 C18. Mobile phase: A 0.1M Triethylammonium acetate (TEAA); B is CH$_3$CN. Analysis was performed with the linear gradient of increase of B from 1-50% in 20 min. Peaks were detected by UV absorption at 254 nm.

FIG. 18: Purity analysis of the pure oligonucleotide ON1 5'-XAC TTG GCT CCA AGT CAC CGT T-3' (SEQ. ID No. 1), where is X is dithiolane modification, after purification of, crude oligo was purified by HPLC on Source 15Q ion-exchange column (1.0 cm×25 cm). Analytical purity of compounds was checked using a Varian Prostar HPLC equipped with ChromSep SS column (4.6×250 mm) and ChromSep Guard-Column OmniSpher 5 C18. Mobile phase: A 0.1M Triethylammonium acetate (TEAA); B is CH$_3$CN. Analysis was performed with the linear gradient of increase of B from 1-50% in 20 min. Peaks were detected by UV absorption at 254 nm.

FIG. 19: HPLC Table peaks pure oligonucleotide ON1 5'-XAC TTG GCT CCA AGT CAC CGT T-3' (SEQ. ID No. 1), where is X is dithiolane modification.

FIG. 20: ESI-MS of the pure ON1 5'-XAC TTG GCT CCA AGT CAC CGT T-3' (SEQ. ID No. 1), where is X is dithiolane modification. Found m/z [M−H]$^-$ 6754 and Calc m/z [M−H]$^-$ 6754.

FIG. 21: Purity analysis of the crude oligonucleotide ON2 5'ACT TGG CTC CAX AGT CAC CGT T-3' (SEQ. ID No. 2), where is X is dithiolane modification after subjecting to three different deprotection conditions viz., a) AMA reagent, 30 min at room temperature then for 1 h at 50° C.; b) aqueous NH$_3$ at 37° C. for 24 h; and c) aqueous NH$_3$ at 50 C for 16 h. Analytical purity of compounds was checked using a Varian Prostar HPLC equipped with ChromSep SS column (4.6×250 mm) and ChromSep Guard-Column OmniSpher 5 C18. Mobile phase: A 0.1M Triethylammonium acetate (TEAA); B is CH$_3$CN. Analysis was performed with the linear gradient of increase of B from 1-50% in 20 min. Peaks were detected by UV absorption at 254 nm.

FIG. 22: Purity analysis of the pure oligonucleotide ON2 5'ACT TGG CTC CAX AGT CAC CGT T-3' (SEQ. ID No. 2), where is X is dithiolane modification, after purification of crude oligo by HPLC on Source 15Q ion-exchange column (1.0 cm×25 cm). Analytical purity of compounds was checked using a Varian Prostar HPLC equipped with ChromSep SS column (4.6×250 mm) and ChromSep Guard-Column OmniSpher 5 C18. Mobile phase: A 0.1M Triethylammonium acetate (TEAA); B is CH$_3$CN. Analysis was performed with the linear gradient of increase of B from 1-50% in 20 min. Peaks were detected by UV absorption at 254 nm.

FIG. 23: HPLC table peaks of the pure oligonucleotide ON2 5'ACT TGG CTC CAX AGT CAC CGT T-3' (SEQ. ID No. 2), where is X is dithiolane modification.

FIG. 24: ESI-MS of the pure ON2 5'ACT TGG CTC CA X AGT CAC CGT T-3' (SEQ. ID No. 2), where is X is dithiolane modification. Found m/z [M−H]$^-$ 6754 and Calc m/z [M−H]$^-$ 6754.

FIG. 25: Purity analysis of the crude oligonucleotide ON3 5'-ACT TGG CTC CAA GTC ACC GTX-3' (SEQ. ID No. 3), where is Xis dithiolane modification, after subjecting to three different deprotection conditions viz. a) AMA reagent, 30 min at room temperature then for 1 h at 50° C.; b) aqueous NH$_3$ at 37° C. for 24 h; and c) aqueous NH$_3$ at 50 C for 16 h. Analytical purity of compounds was checked using a Varian Prostar HPLC equipped with ChromSep SS column (4.6×250 mm) and ChromSep Guard-Column OmniSpher 5 C18. Mobile phase: A 0.1M Triethylammonium acetate (TEAA); B is CH$_3$CN. Analysis was performed with the linear gradient of increase of B from 1-50% in 20 min. Peaks were detected by UV absorption at 254 nm.

FIG. 26: Purity analysis of the pure oligonucleotide ON3 5'-ACT TGG CTC CAA GTC ACC GTX-3' (SEQ. ID No. 3), where is Xis dithiolane modification, after purification of crude oligo by HPLC on Source 15Q ion-exchange column (1.0 cm×25 cm). Analytical purity of compounds was checked using a Varian Prostar HPLC equipped with ChromSep SS column (4.6×250 mm) and ChromSep Guard-Column OmniSpher 5 C18. Mobile phase: A 0.1M Triethylammonium acetate (TEAA); B is $CH_3CN$. Analysis was performed with the linear gradient of increase of B from 1-50% in 20 min. Peaks were detected by UV absorption at 254 nm.

FIG. 27: HPLC Table peaks the pure oligonucleotide ON3 5'-ACT TGG CTC CAA GTC ACC GTX-3' (SEQ. ID No. 3), where is Xis dithiolane modification.

FIG. 28: ESI-MS of the pure ON3 5'-ACT TGG CTC CAA GTC ACC GTX-3' (SEQ. ID No. 3). Found m/z [M-H]⁻ 6450 and Calc m/z [M-H]⁻ 6450.

DETAILED DESCRIPTION OF THE INVENTION

The thiol modified oligonucleotides have vast number of applications in the field of nucleic acid chemistry such as it enables covalent attachment of a variety of ligands and also has an ability to form relatively stronger bond with gold surface. DNA functionalized gold nanoparticles have become widely used building blocks in key nucleic acid based assembly strategies and therapeutics. Even though thiol group forms relatively stronger bond with elemental gold (about 30-40 Kcal/mole), it gets displaced at higher temperature, in high salt concentration buffers and in presence other thiols. For many of applications with these conjugates strong binding of the oligonucleotides to the gold nano particles is required. However to circumvent displacement of thiol, a few cyclic disulfide modifiers that can introduce multiple thiol groups have been introduced in the priorart. Their stability studies revealed that these multi-thiol functionalized oligonucleotides form relatively more stable SAMs compared to the corresponding mono-thiol derivatives. In the present application, we describe the design and efficient synthesis of cyclic dithiolane phosphoramidite derivative 1 (Chart 1) and corresponding dithiolane succinyl CPG supports 2 (Chart 1).

Synthesis of target dithiolane phosphoramidite monomer 1 and corresponding supports 2 was straight forward and shown in Scheme 1. Deprotection of Fmoc group of the compound 5, which is synthesized by following previously reported protocol, [Nelson, P. S., Kent, M., Muthini, S, *Nucleic Acids Res.* 1992 20, 6253-6259] was achieved by treating it with saturated $MeOH/NH_3$ for overnight in a sealed glass bottle to afford free amine compound 6 in 85% yield. Amine 6 was coupled to commercially available thioctic acid by following EDC mediated coupling protocol to get intermediate 7 in 77% yield. Synthesis of final phosphoramidite derivative 1 was carried out with N,N'-(diisopropyl)-phosphoramidochloridite and Hunig's base at lower temperature (ice-cold water bath) with simultaneous deoxygenation by purging argon into reaction mixture. To synthesize CPG solid supports with dithiolane derivatives, free hydroxy of compound 7 was succinilyted using succinicanhydride, 4-dimethylaminopyridine in pyridine at 37° C. for overnight to get the pyridinum salt of succinate 8 in 62% yield. Finally, succinate 8 was coupled to free amine group of 1000 Å CPG with long chain alkyl amino spacer arm to afford corresponding supports with dithiolane derivatives 10. Unlike acyclic disulfide thiol modifiers, these cyclic dithiolane based phosphoramidite monomers and supports have an advantage to introduce thiol groups at 5'- or 3'- or any site of the oligonucleotide sequence.

Scheme 1: Synthesis of dithiolane phosphoramidites and solid supports

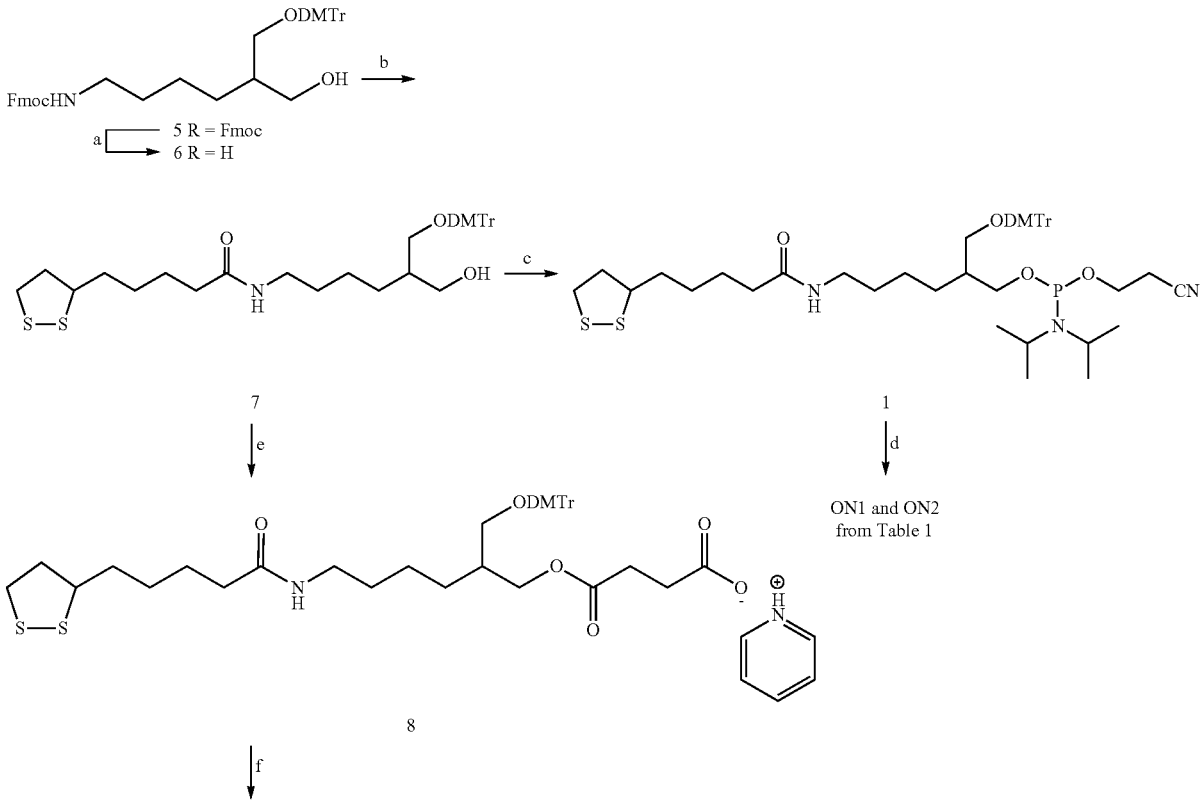

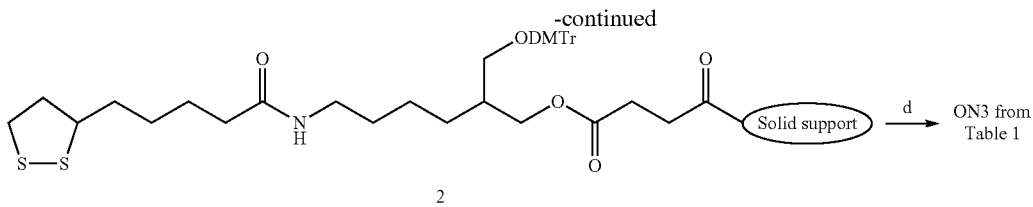

Reagents and Conditions: a) 20% NH₃ in MeOH, rt, 16 h, 85%; b) Thioctic acid, EDC.HCl, N,N'-dimethylformamide, rt, 77%; c) 2-Cyanoethyl N,N'-(diisopropyl)phosphoramidochloridite, N,N'-diisopropylethylamine, anhydrous THF, 0 C to rt, 63%; d) DNA synthesizer; e) Succinic anhydride, 4-dimethylaminopyridine, anhydrous pyridine, rt to 37° C., 62%; f) HBTU, N,N'-diisopropylethylamine, CPG-long chain alkyl amine spacer, rt to 37° C.

With these monomers in our hand, we have synthesized three oligonucletide sequences with incorporation of modification at 3'- or 5'- or in the middle of the sequence (ON1-ON3, SEQ. ID No. 1-3, Table 1). Incorporation of dithiolane phosphoramidite monomer 1 into 21-mer mixed base sequence oligonucleotide was performed on a 1 μmol scale using an automated DNA synthesizer. Standard procedures were applied except for extended coupling time of 15 min and using 5-(ethylthio)tetrazole as catalyst for dithiolane phosphoramidites 1.

To check the compatibility of this dithiolane modification attached to oligonucleotides, various deprotection conditions were carried out. Some of the conditions are outlined as follows, viz., standard deprotection protocols, a) AMA reagent (concentrated ammonia/40% aqueous methylamine 1/1, v/v), 30 min at room temperature then for 1 h at 50° C.; b) aqueous NH₃ at 37° C. for 24 h; and c) aqueous NH₃ at 50° C. for 16 h. Among the different conditions, purity of oligonucleotides that are deprotected by conditions of aqueous NH₃ was around 75-80%. However, purity of oligo from the AMA reagent deprotection condition was around 50-60% and substantial amounts of other impurities (30%) were generated during these deprotection conditions (Table 1, FIG. 17 for ON1 (SEQ. ID No. 1), FIG. 21 for ON2 (SEQ. ID No. 2) and FIG. 25 for ON3 (SEQ. ID No. 3). It clearly indicates non-compatibility of AMA reagent with dithiolane modification. After deprotecting oligos with aqueous NH₃ 16 h at 50° C., crude oligo was purified by HPLC on Source 15Q ion-exchange column (1.0 cm×25 cm). Oligo was eluted using gradient buffer A (1 M Tris base:methanol:H₂O, 5:10:85, v/v/v) and buffer B (0.5 M aqueous NaClO₄) with a linear 0-90% buffer B gradient over 40 min. Desired oligonucleotide was collected by monitoring at 295 nm and precipitated by adding 5.0 vol of 2% LiClO₄ in acetone. Analytical purity of compounds was checked using a Varian Prostar HPLC equipped with ChromSep SS column (4.6× 250 mm) and ChromSep Guard-Column OmniSpher 5 C18 with peak detection detected by UV absorption at 254 nm. Mobile phase: A 0.1M Triethylammonium acetate (TEAA); B is CH₃CN. Analysis was performed with the linear gradient of increase of B from 1-50% in 20 min. Peaks were detected by UV absorption at 254 nm. The exact composition of oligonucleotides ON1-ON3 (SEQ. ID No. 1-3) was verified by ESI-MS analysis (Table 1).

TABLE 1

ESI 1: Purity of crude ONs using three different deprotection conditions and after purification of crude ON by HPLC on Source 15Q ion-exchange column, ESI-MS of ONs with dithiolane modifications.

| | | Purity of Crude ON[a] in % | | | Purity[a] after purification in % | Found/Calcd m/z [M-H]⁻ |
|---|---|---|---|---|---|---|
| | | | Aq NH₃ | | | |
| | ON Sequence | AMA reagent | 37 C. 24 h | 55 C. 16 h | | |
| 1 | 5'-XAC TTG GCT CCA AGT CAC CGT T (SEQ. ID No. 1) | 52 | 66 | 65 | 88 | 6754/6754 |
| 2 | 5'ACT TGG CTC CAX AGT CAC CGT T (SEQ. ID No. 2) | 67 | 85 | 85 | 94 | 6754/6754 |
| 3 | 5'-ACT TGG CTC CAA GTC ACC GTX (SEQ. ID No. 3) | 65 | 79 | 75 | 97 | 6450/6450 |

[a]Purity was checked using a Varian Prostar RP HPLC equipped with C18 ChromSep SS column (4.6 × 250 mm).
"X" is dithiolane modification Stability analysis of SAMs formed by these dithiolane modified oligonucleotides on the gold surface has been carried out using the following procedure that is reported by Letsinger et. al [Letsinger, R. L., Elghanian, R., Viswanadham, G., Mirkin, C. A. *Bioconj. Chem.* 2000, 11, 289]. This procedure involves the following steps:

(1) Synthesis of oligonucleotides with multiple incorporation of dithiolane and also corresponding oligos with acyclic disulfide moieties as control;

(2) Generating reactive thiol groups on both of these oligos by reducing them with 0.1 M DTT;

(3) Chemisorption of these oligos onto the commercially available 5 nm diameter gold nano particles and (4) Stability analysis of these SAMs in the presence of DTT by following the procedure reported by Letsinger et. al [Letsinger, R. L., Elghanian, R., Viswanadham, G., Mirkin, C. A. *Bioconj. Chem.* 2000, 11, 289].

From results reported by other, we anticipate that SAMs generated by the two reactive thiols of dithiolane should be more stable than the corresponding SAMs formed by mono-thiol derivatives.

In addition to the above specific dithiolane amidite 1 and corresponding solid supports 2 (Chart 1), this technology can also be applied to the various other dithiolane amidites and solid supports with the different linker chemistry, linker length as describe in the following paragraphs. All these molecules can be synthesized using the similar synthetic stratagy that was described in Scheme 1. The following is the clear description about these molecules.

According to an embodiment, the invention is directed to a dithiolane compound that can be represented by Formula I:

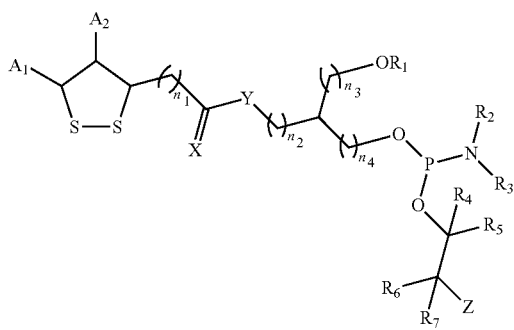

Formula I wherein:

X and Y are independently oxygen (O), sulfur (S), selenium (Se), NH or N—R where R is straight or branched alkyl chain of 0 to 20 carbon atoms;

$n_1$, $n_2$, $n_3$ and $n_4$ are independently straight or branched alkyl chain of 0 to 20 carbon atoms;

$R_1$ is hydrogen (H) atom, a member selected from the group consisting of acid labile hydroxyl protecting group, or selected from the group consisting of triphenylmethyl (trityl), monomethoxytriphenylmethyl (MMTr), dimethoxytriphenylmethyl (DMTr) trimethoxytriphenylmethyl (TMTr), di-p-anisylphenylmethyl, p-fluorophenyl-1-naphthylphenylmethyl, p-anisyl-1-naphthylphenylmethyl, di-o-anisyl-1-naphthylmethyl, di-o-anisylphenylmethyl, p-tolyldiphenylmethyl, di-p-anisylphenylmethyl, di-o-anisyl-1-naphthylmethyl, di-p-anisylphenylmethyl, di-o-anisylphenylmethyl or p-tolyl diphenyl methyl, tetrahydropyranyl and methoxytetrahydropyranyl, $R_1$ is a mild base deprotecting group such as benzoyl, acetyl, phenoxy acetyl, substituted benzoyl, $R_1$ is a photo cleavable protecting group such as a member selected from the group consisting of NPPOC (3'-nitrophenylpropyloxycarbonyl), NVOC (6-nitroveratryloxycarbonyl), MeNPOC (a-methyl-2-nitropiperonyloxycarbonyl), and MNPPOC (2-(3,4-methylenedioxy-6-nitrophenyl) propoxycarbonyl;

$R_2$ and $R_3$ are independently alkyl group or aromatic group;

$R_2$, $R_3$, $R_4$, $R_5$, $R_6$ and $R_7$ independently hydrogen (H), primary, secondary, or tertiary alkyl group;

$A_1$ and $A_2$ are independently hydrogen (H), primary, secondary, or tertiary alkyl group; and Z is hydrogen (H) atom, or a nitrile (CN) group.

Preferably, the dithiolane compound according to Formula I may have the following attributes, wherein:

$n_1$ and $n_2$=4, $n_3$ and $n_4$=1, $A_1$, and $A_2$ are hydrogen (H) atom,

X=O, Y=NH $R_1$ is a dimethoxytrityl (DMTr) group, $R_2$ and $R_3$ are isopropyl, $R_4$, $R_5$, $R_6$ and $R_7$ are hydrogen (H) atoms, Z represents the nitrile (CN) group, and the dithiolane compound can be represented by Formula II:

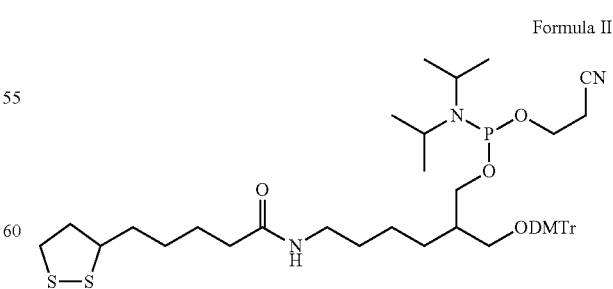

Formula II

According to another embodiment, the invention is directed to a dithiolane compound on solid support represented by Formula III:

Formula III

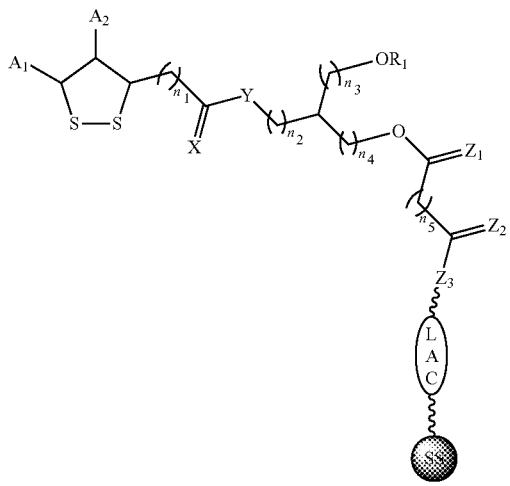

wherein:

X and Y are independently oxygen (O), sulfur (S), selenium (Se), NH or N—R where R is straight or branched alkyl chain of 0 to 20 carbon atoms.

$n_1$, $n_2$, $n_3$, and $n_4$ are independently straight or branched alkyl chain of 0 to 20 carbon atoms.

$n_5$ is succinyl, oxalyl or hydroquinolinyl $R_1$ is hydrogen (H) atom or a member selected from the group consisting of acid labile hydroxyl protecting group, or selected from the group consisting of triphenylmethyl (trityl), monomethoxytriphenylmethyl (MMTr), dimethoxytriphenylmethyl (DMTr) trimethoxytriphenylmethyl (TMTr), di-p-anisylphenylmethyl, p-fluorophenyl-1-naphthylphenylmethyl, p-anisyl-1-naphthylphenylmethyl, di-o-anisyl-1-naphthylmethyl, di-o-anisylphenylmethyl, p-tolyldiphenylmethyl, di-p-anisylphenylmethyl, di-o-anisyl-1-naphthylmethyl, di-p-anisylphenylmethyl, di-o-anisylphenylmethyl or p-tolyl diphenyl methyl, tetrahydropyranyl and methoxytetrahydropyranyl, $R_1$ is a mild base deprotecting group such as benzoyl, acetyl, phenoxy acetyl, substituted benzoyl, $R_1$ is a photo cleavable protecting group such as a member selected from the group consisting of NPPOC (3'-Nitrophenylpropyloxycarbonyl), NVOC (6-nitroveratryloxycarbonyl), MeNPOC (a-methyl-2-nitropiperonyloxycarbonyl), and MNPPOC (2-(3,4-methylenedioxy-6-nitrophenyl) propoxycarbonyl;

$Z_1$ and $Z_2$ are independently oxygen (O), sulfur (S) or selenium (Se);

$Z_3$ is NH or N—R, where R is straight or branched alkyl chain of 0 to 20 carbon atoms;

LAC is a long alkyl chain;

$A_1$ and $A_2$ are independently hydrogen (H), primary, secondary or tertiary alkyl groups;

SS is a solid support such as controlled pore glass (CPG) or polystyrene.

Preferably, the dithiolane compound of Formula III may have the following attributes, wherein;

$n_1$ and $n_2$=4, $n_3$ and $n_4$=1, $n_5$=2,

X=O, Y=NH, $Z_1$ and $Z_2$ are oxygen (O) atoms, $Z_3$ represents NH, $R_1$ is dimethoxytrityl (DMTr) group, LCAA is a long alkyl chain with C18 spacer, SS is CPG solid support, and the dithiolane compound on solid support can be represented by Formula IV:

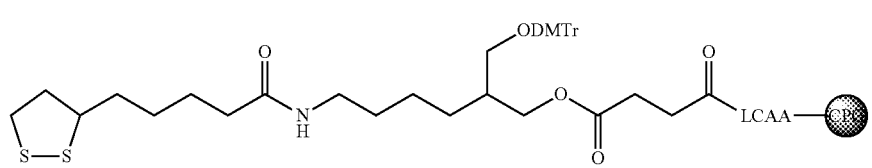

Formula IV

According to another embodiment, the invention is directed to a process of synthesizing the dithiolane compound of Formula I as follows:

(1) In order to make compounds of Formula ZZ, activation the compound of Formula XX can be performed using suitable activating agent followed by coupling with compound of Formula YY under suitable conditions.

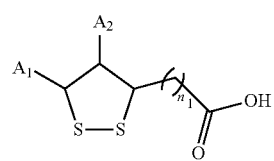

Formula XX

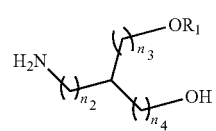

Formula YY

Formula ZZ

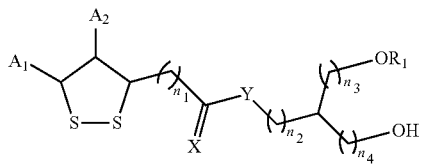

(2) The free hydroxyl group of the compound of Formula ZZ can be functionalized to corresponding phosphoramidite of Formula I using the phosphorylating reagent such as compound of Formula UU under standard conditions.

Formula UU

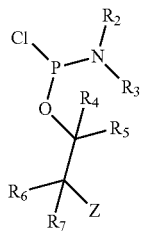

(2) The free hydroxyl group of the compound of Formula ZZ can further be functionalized to corresponding succinates of Formula WW using succinic anhydride, oxalyl active ester and hydroquinolinyl active ester and standard reaction conditions to generate the succinates. Subsequently, the compounds of Formula WW can be derivatized on to suitable solid supports using standard reaction conditions to obtain the compounds of Formula III:

Formula WW

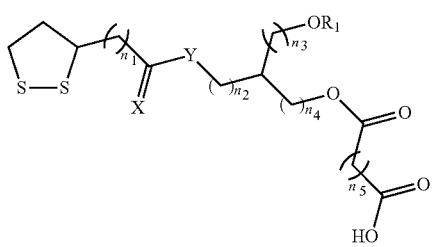

where $n_5$ is the succinate, oxalyl and hydroquinolinyl.

Furthermore, according to another embodiment of the invention, the invention is directed to an oligonucleotide having a dithiolane function such as represented Formulas V-I, Formula V-II or Formula V-III:

Formula V-I

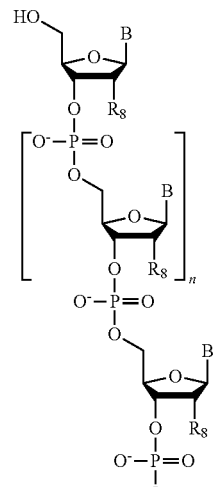

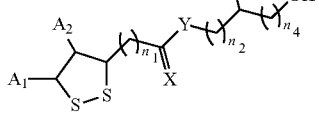

Formula V-II

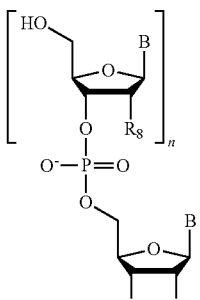

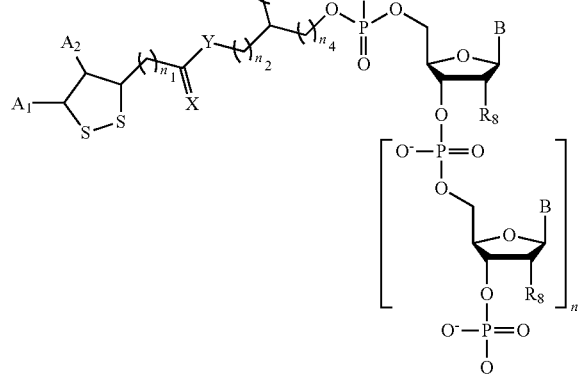

-continued

Formula V-III

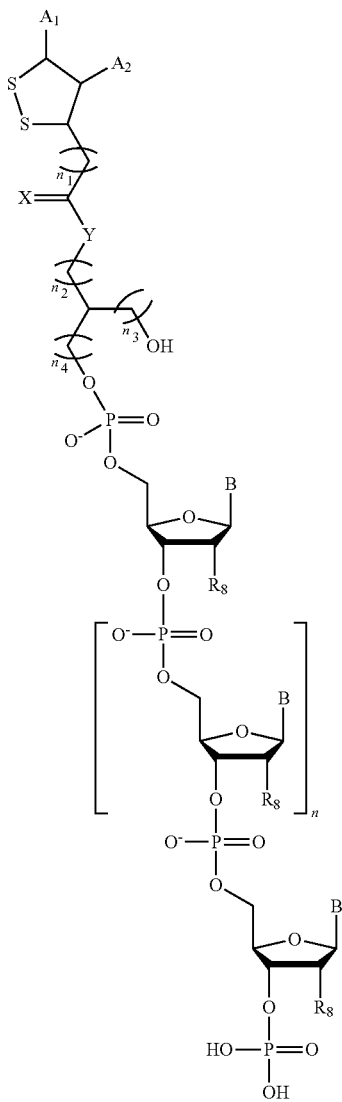

wherein:

B is a nucleoside base selected from the group consisting of adenine, cytosine, guanosine and uracil, inosine, 5-methyl cytosine, 5-methyl uracil, 5-fluoro uracil, 7-deazaadenine, 7-deazaguanine, a modified purine and 5-fluoro cytosine, or a non-nucleoside moiety;

n is a number between 0 and 200; and $R_8$ is H, OH, methyl, ethyl, propyl or higher alkyl group, a propyl amino group, fluoro, or fluoro arabinose.

With respect to the oligonucleotides described in Table 1, ON1 (SEQ. ID No. 1) can be represented schematically by Formula V-III. On the other hand, ON2 (SEQ. ID No. 2) can be represented schematically by Formula V-II, and ON2 (SEQ. ID No. 3) by Formula V-I.

According to another embodiment, the invention is directed to a process of synthesizing the oligonucleotide having the dithiolane function as represented by one of Formula V-I, Formula V-II, or Formula V-III, comprising the step of deprotecting the oligonucleotide with treatment of appropriate base to remove protecting groups at a suitable temperature.

According to another embodiment, the invention is directed to an oligonucleotide conjugate on an inert solid surface represented by Structure I.

Structure I

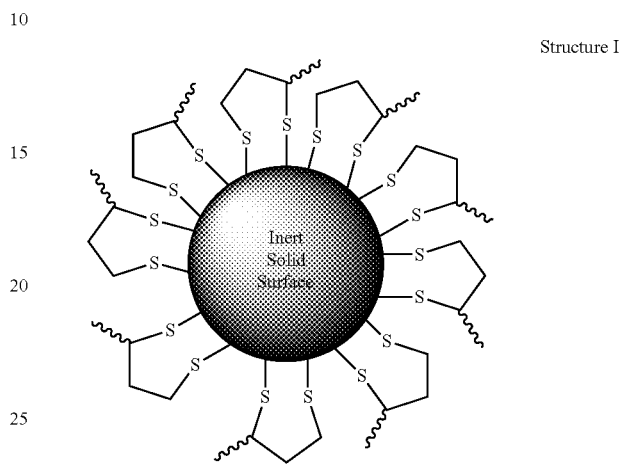

Preferably, the oligonucleotide conjugate on the inert solid surface, and the inert solid surface is gold, silver or quantum dots.

All reagents and solvents were of analytical grade and obtained from commercial suppliers and used without further purification. The low level of water content of anhydrous solvents was verified by a Karl-Fischer apparatus. Reactions were conducted under an atmosphere of argon whenever anhydrous solvents were used. All reactions were monitored by thin-layer chromatography (TLC) using silica gel coated plates with a fluorescence indicator which were visualized under UV light. Silica gel column chromatography was performed with Silica gel 60 (particle size 0.063-0.200 mm, Merck). Evaporation of solvents was carried out under reduced pressure at a temperature below 40° C. After column chromatography, appropriate fractions were pooled, evaporated and dried at high vacuum for at least 12 h to give the obtained products in high purity (>95%), unless stated otherwise. $^1$H NMR, and/or $^{31}$P NMR analytical HPLC ascertained sample purity. No corrections in yields were made for solvent of crystallization. $^1$H NMR, and/or $^{31}$P NMR spectra were recorded at 500 and 202 MHz respectively. Chemical shifts are reported in parts per million (ppm) relative to tetramethylsilane or deuterated solvent as the internal standard (δH: CDCl$_3$ 7.26 ppm). Traces of solvents in NMR spectra were identified by reference to published data. [Gottlieb, H. E.; Kotlyar, V.; Nudelman, A. *J. Org. Chem.* 1997, 62, 7512-7515]. ESI/MS analysis was carried on Perkin Elmer PE-SCIEX API-150 mass spectrometer.

EXAMPLE 1

S6-amino-2-((bis(4-methoxyphenyl)(phenyl)methoxy)methyl)hexan-1-ol (6)

Compound 1 (10 g, 14.9 mmol) was dissolved in 20% $NH_3$ in MeOH (100 mL) in a sealed bottle. After stirring the reaction at room temperature for 16 h, it was evaporated to dryness and purified by silica gel column chromatography using (0-20% MeoH in $CHCl_3$) with 1% triethylamine throughout the column to afford the target compound 6 (5.7 g, 85%). $R_f$=0.1 (10% Methanol in Chloroform, v/v). HPLC analysis single peak at 4.62 min (45 to 98% acetonitrile in 0.1M TEAA buffer) and purity is 99.34%.

EXAMPLE 2

N-(6-(bis(4-methoxyphenyl)(phenyl)methoxy)-5-(hydroxymethyl)hexyl)-5-(1,2-dithiolan-3-yl)pentanamide (7)

Thioctic acid (2.4 g, 11.8 mmol) was suspended in anhydrous N,N'-dimethylformamide (30 mL) and EDC.HCL (3.45 g, 18.2 mmol) was added to this. After stirring the reaction for 30 min, clear solution was obtained. Amine compound 6 (4.1 g, 9.1 mmol) was added to this at room temperature. After stirring the reaction for 16 h at room temperature, it was evaporated to dryness and purified by silica gel column chromatography using (80-100% EtOAC in hexane) to afford the target compound 7 (4.5 g, 77%). $R_f$=0.5 (EtOAc); MS m/z $C_{36}H_{47}NO_5S_2$+Na ([M+Na]$^+$ 660.29, calcd 660.8); $^1$H NMR ($CDCl_3$) 8.01 (s, 1H), 7.23-7.42 (m, 9H), 6.80-6.85 (m, 4H), 5.43 (s, 1H), 3.79 (s, 6H), 3.53-3.79 (m, 2H), 3.08-3.26 (m, 5H), 2.60-2.68 (m, 1H), 2.41-2.62 (m, 2H), 2.23-2.30 (m, 1H), 2.10-2.16 (m 2H), 1.80-1.93 (m, 2H), 1.60-1.76 (m 4H), 1.41-1.52 (m, 2H), 1.11-1.40 (m, 6H). HPLC analysis single peak at 14.41 min (45 to 98% acetonitrile in 0.1M TEAA buffer) and purity is 99.48%.

EXAMPLE 3

6-(5-(1,2-dithiolan-3-yl)pentanamido)-2-((bis(4-methoxyphenyl)(phenyl)methoxy)methyl)hexyl 2-cyanoethyl diisopropylphosphoramidite (1)

DMT-dithiolane coupled compound 7 (3.3 g, 5.1 mmol) was dried by coevaporation with anhydrous $CH_3CN$ (1×100 mL) and dried over-night on high vacuum pump then dissolved in anhydrous THF (50 mL). To this was added N,N'-diisopropylethylamine (2.7 mL, 15.5 mmol) and cooled in an ice cold water bath. After bubbling the argon for 25 min, 2-cyanoethyl N,N'-(diisopropyl)phosphoramidochloriditi (1.27 mL, 5.69 mmol) was added under complete argon atmosphere and the reaction mixture was stirred in ice-cold water bath for 1 h, whereupon it was diluted with EtOAc (100 mL). The organic phase was washed with saturated aqueous $NaHCO_3$ (100 mL), and saturated aqueous NaCl (100 ml). The combine aqueous phase was back-extracted with EtOAc (250 mL). The combined organic phase was evaporated to dryness, and the resulting residue was purified by silica gel column chromatography (45:45:10 Heane:EtOAc:Triethylamine, v/v/v) to afford target amidite 1 (2.7 g, 63%) as an color less oil. $R_f$=0.5 (EtOAc:Hexane:Triethylamine, 45:45:10, v/v/v). MS m/z $C_{45}H_{64}N_3O_6PS_2$.Na ([M+Na]$^+$ 860.40, calcd 860.90). $^1$H NMR ($CDCl_3$) 7.19-7.43 (m, 9H), 6.77-6.85 (m, 4H), 5.47 (s, 1H), 3.79 (s, 6H), 3.54-3.77 (m, 4H), 3.11-3.17 (m, 4H), 2.42-2.60 (m, 3H), 2.11-2.15 (m, 2H), 1.80-1.92 (m, 2H), 1.63-1.69 (m, 4H), 1.31-1.52 (m, 6H), 1.18-1.28 (m, 3H), 1.18-1.27 (m, 12H). HPLC analysis single peak at 11.84 min (80-100% acetonitrile in 0.1M TEAA buffer) and purity is 97.21%. $^{31}$P NMR ($CDCl_3$) 147.92, 147.75.

EXAMPLE 4

4-(6-(5-(1,2-dithiolan-3-yl)pentanamido)-2-((bis(4-methoxyphenyl)(phenyl)methoxy) methyl)hexyloxy)-4-oxobutanoate (8)

DMT-dithiolane coupled compound 7 (900 mg, 1.41 mmol) was dissolved in anhydrous pyridine (10 mL) and 4-dimethylaminopyridine (DMAP, 35 mg, 0.29 mmol) and succinic anhydride (290 mg, 2.9 mmol) were added to this. After stirring the reaction for 20 m in at room temperature, reaction was moved to 37 C for 16 h. Then reaction mixture was cooled in ice cold water bath and quenched with $H_2O$ (1 mL) and evaporated to dryness. The resulting reaction mixture was dissolved in EtOAc (100 mL) and washed with $H_2O$ (1×25 mL). Aqueous phase back extracted with EtoAC (1×50 mL) and combined organic phases were evaporated till dryness. The resulting crude residue was purified by the silica gel column chromatography (0-3% MeOH in EtoAc) with 1% pyridine throughout the column to afford the target succinate 8 as a pyridinium salt (700 mg, 62%). $R_f$=0.7 (MeOH:EtOAc:Pyridine, 5:94.5:0.5, v/v/v). MS m/z $C_{40}H_{50}NO_8S_2$.Na ([M+Na]$^+$ 759.98, calcd 759.8). $^1$H NMR ($CDCl_3$) 8.62 (m, 1H), 7.19-7.43 (m, 9H), 6.77-6.85 (m, 4H), 5.62 (s, 1H), 4.26-4.29 (m, 1H), 4.13-4.17 (m, 1H), 3.79 (s, 6H), 3.51-3.60 (m, 1H), 3.01-3.19 (m, 4H), 2.48-2.60 (m, 6H), 2.15-2.30 (m, 2H), 1.90-1.98 (m, 2H), 1.53-1.62 (m, 4H), 1.28-1.48 (m, 6H), 1.11-1.25 (m, 4H). HPLC analysis single peak at 9.15 min (45-98% acetonitrile in 0.1M TEAA buffer) and purity is 96.6%.

EXAMPLE 5

Procedure for Coupling of Succinate Derivative 9 with Free Amine of CPG

The succinate compound 8 (150 mg, 0.203 mmol) was dissolved in anhydrous $CH_3CN$ (30 mL) and O-Benzotriazole-N,N,N',N'-tetramethyl-uronium-hexafluoro-phosphate (HBTU, 85 mg, 0.224 mmol) was added to this. After standing this mixture for 10 min at room temperature, it was added to CPG with amine loading (1000 Å, 3.5 g, 98 μmol/gr). After shaking thoroughly, N,N-Diisopropylethylamine (72 μL, 0.406 mmol) was added to this slurry of reaction mixture and allowed to stand at 37° C. for 16 h, CPG was filtered and washed sequentially with N,N-dimethylformamide (1×25 mL), CH$_3$CN (1×25 mL), MeOH (1×25 mL), isopropanol (1×25 mL) and finally with ether (1×25 mL). The resulting CPG was dried at room temperature for 24 h then unreacted amines were capped using CAP A solution (20 mL, THF:Pyridine:Aceticanhydride, 80:10:10, v/v/v). After standing the reaction for 4 h at room temperature, CPG was filtered and washed sequentially with isopropanol (1×25 mL), 10% triethylamine in isopropanol (2×25 mL), isopropanol (2×25 mL), and finally with ether (1×25 mL). The resulting CPG was dried at room temperature for 24 h to afford CPG (2.7 g, 43.1 μmol/g) attached with dithiolane derivative.

What is claimed is:

1. An oligonucleotide having a dithiolane function represented by one of Formula V-I, Formula V-II or Formula V-III:

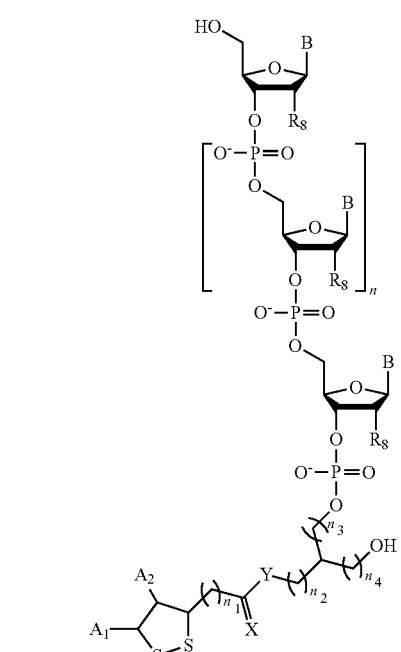

Formula V-I

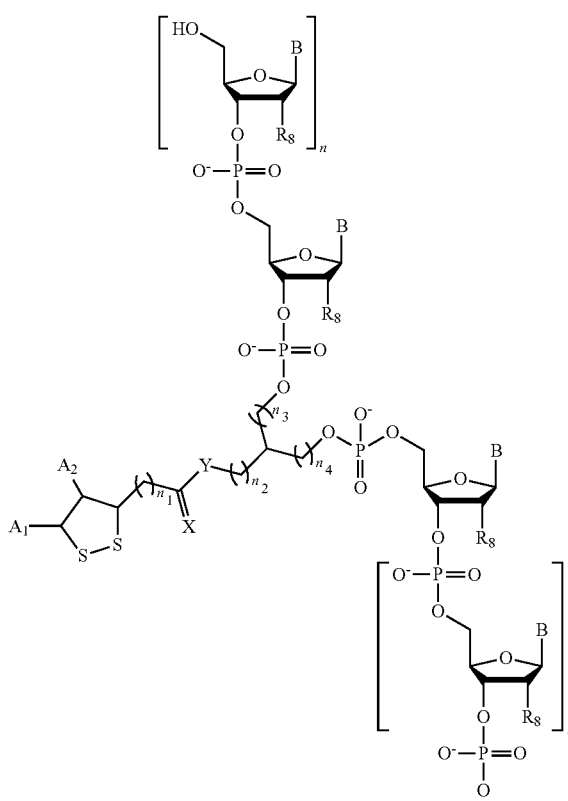

Formula V-II

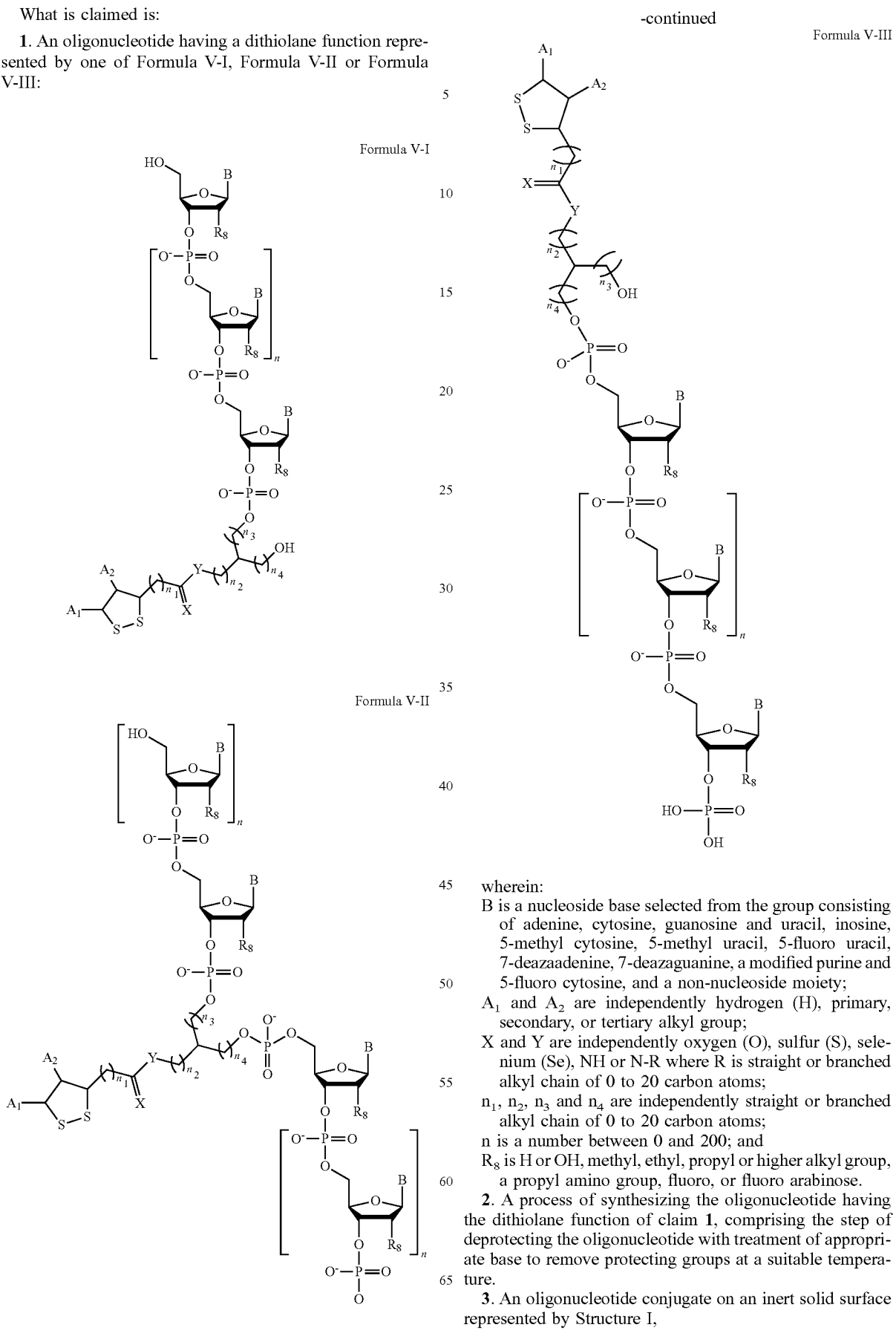

Formula V-III wherein:
B is a nucleoside base selected from the group consisting of adenine, cytosine, guanosine and uracil, inosine, 5-methyl cytosine, 5-methyl uracil, 5-fluoro uracil, 7-deazaadenine, 7-deazaguanine, a modified purine and 5-fluoro cytosine, and a non-nucleoside moiety;
$A_1$ and $A_2$ are independently hydrogen (H), primary, secondary, or tertiary alkyl group;
X and Y are independently oxygen (O), sulfur (S), selenium (Se), NH or N-R where R is straight or branched alkyl chain of 0 to 20 carbon atoms;
$n_1$, $n_2$, $n_3$ and $n_4$ are independently straight or branched alkyl chain of 0 to 20 carbon atoms;
n is a number between 0 and 200; and
$R_8$ is H or OH, methyl, ethyl, propyl or higher alkyl group, a propyl amino group, fluoro, or fluoro arabinose.

2. A process of synthesizing the oligonucleotide having the dithiolane function of claim 1, comprising the step of deprotecting the oligonucleotide with treatment of appropriate base to remove protecting groups at a suitable temperature.

3. An oligonucleotide conjugate on an inert solid surface represented by Structure I, Structure I
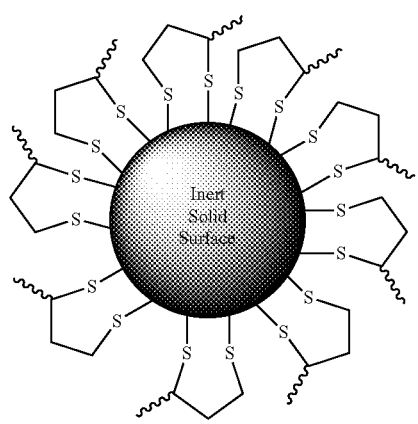
wherein each of ︵︵︵︵︵︵ is a symbol representing an oligonucleotide.
4. The oligonucleotide conjugate on the inert solid surface of claim 3, wherein the inert solid surface is gold, silver or quantum dots.
* * * * *

SEQUENCE LISTING

<160> NUMBER OF SEQ ID NOS: 3

<210> SEQ ID NO 1
<211> LENGTH: 21
<212> TYPE: DNA
<213> ORGANISM: Artificial Sequence
<220> FEATURE:
<223> OTHER INFORMATION: Synthesized
<220> FEATURE:
<221> NAME/KEY: misc_feature
<222> LOCATION: (1)..(1)
<223> OTHER INFORMATION: Dithiolane function is attached to first
      nucleotide

<400> SEQUENCE: 1
acttggctcc aagtcaccgt t                                            21

<210> SEQ ID NO 2
<211> LENGTH: 21
<212> TYPE: DNA
<213> ORGANISM: Artificial Sequence
<220> FEATURE:
<223> OTHER INFORMATION: Synthesized
<220> FEATURE:
<221> NAME/KEY: misc_feature
<222> LOCATION: (11)..(12)
<223> OTHER INFORMATION: Dithiolane function is between 11th and 12th
      nucleotides

<400> SEQUENCE: 2
acttggctcc aagtcaccgt t                                            21

<210> SEQ ID NO 3
<211> LENGTH: 20
<212> TYPE: DNA
<213> ORGANISM: Artificial Sequence
<220> FEATURE:
<223> OTHER INFORMATION: Synthesized
<220> FEATURE:
<221> NAME/KEY: misc_feature
<222> LOCATION: (20)..(20)
<223> OTHER INFORMATION: Dithiolane function is attached to the terminal
      nucleotide

<400> SEQUENCE: 3
acttggctcc aagtcaccgt                                              20